US010117923B2

(12) United States Patent
Ivanov et al.

(10) Patent No.: US 10,117,923 B2
(45) Date of Patent: Nov. 6, 2018

(54) PRODUCTION OF AN IMMUNOGEN USING A PLANT VIRUS

(71) Applicant: Vacplanta Limited, Dublin OT (IE)

(72) Inventors: Petr Alexeevich Ivanov, Moscow (RU); Tatiana Vladimirovna Gasanova, Moscow (RU); Natalia Vitalievna Petukhova, Moscow (RU)

(73) Assignee: VACPLANTA LIMITED, Dublin (IE)

( * ) Notice: Subject to any disclaimer, the term of this patent is extended or adjusted under 35 U.S.C. 154(b) by 0 days.

(21) Appl. No.: 15/607,189

(22) Filed: May 26, 2017

(65) Prior Publication Data

US 2017/0258886 A1 Sep. 14, 2017

Related U.S. Application Data

(63) Continuation-in-part of application No. 14/429,264, filed as application No. PCT/US2013/068486 on Nov. 5, 2013.

(60) Provisional application No. 61/723,704, filed on Nov. 7, 2012.

(51) Int. Cl.

| | |
|---|---|
| ***A61K 39/12*** | (2006.01) |
| ***C07K 14/005*** | (2006.01) |
| ***C12N 15/82*** | (2006.01) |
| *C12N 15/87* | (2006.01) |
| *A61K 39/00* | (2006.01) |

(52) U.S. Cl.

CPC ............ *A61K 39/12* (2013.01); *C07K 14/005* (2013.01); *C12N 15/8258* (2013.01); *A61K 2039/5256* (2013.01); *A61K 2039/5258* (2013.01); *C07K 2319/40* (2013.01); *C12N 2760/16134* (2013.01); *C12N 2770/00023* (2013.01); *C12N 2770/00043* (2013.01)

(58) Field of Classification Search

CPC .......... A61K 39/145; A61K 2039/5258; A61K 2039/517; C12N 2730/10123; C12N 2770/16023; C12N 2770/32423; C12N 2795/10123

See application file for complete search history.

(56) References Cited

U.S. PATENT DOCUMENTS

| | | | |
|---|---|---|---|
| 7,361,352 | B2 | 4/2008 | Birkett et al. |
| 7,939,318 | B2 | 5/2011 | McCormick et al. |
| 8,889,144 | B2 | 11/2014 | Champion et al. |
| 2006/0115489 | A1 | 6/2006 | Birkett et al. |
| 2009/0062514 | A1 | 3/2009 | Werner et al. |
| 2009/0117144 | A1 | 5/2009 | Rasochova et al. |
| 2010/0111996 | A1 | 5/2010 | Leclerc |

OTHER PUBLICATIONS

Adam, et al. "Virgaviridae: a new family of rod-shaped plant viruses", Arch Virol (2009) 154:1967-1972.
Bendahmane, et al. "Display of Epitopes on the Surface of Tobacco Mosaic Virus: Impact of Charge and Isoelectric Point of the Epitope on Virus-Host Interactions", J. Mol. Biol. (1999) 290, 9-20.
De Filette, et al., "An Influenza A Vaccine Based on Tetrameric Ectodomain of Matrix Protein 2", The Journal of Biological Chemistry, 2008, 283(17): 11382-11387.
Dunoyer, et al. "Peanut Clump Virus RNA-1-Encoded P15 Regulates Viral RNA Accumulation but Is Not Abundant at Viral RNA Replication Sites", Journal of Virology, 2001, pp. 1941-1948.
Helias, et al. "Production of recombinant Potato mop-top virus coat protein in *Escherichia coli* and generation of antisera recognising native virus protein", Journal of Virological Methods ,110 (2003) 91-97.
Kendall, et al. "Barley stripe mosaic virus: structure and relationship to the tobamoviruses", Virology, 2013, 443(2):265-270.
Koo, et al., "Protective immunity against murine hepatitis virus (MHV) induced by intranasal or subcutaneous administration of hybrids of tobacco mosaic virus that carries an MHV epitope", Proc. Natl. Acad. Sci. USA, 1999, 96:7774-7779.
Liu, et al. "Functional Replacement of the Tobacco rattle virus Cysteine-rich Protein by Pathogenicity Proteins from Unrelated Plant Viruses", Virology 298, 232-239 (2002).
Mayo, et al. "Developments in the understanding of the particle structure of tobraviruses", Biochimie, 1993, 75(8):639-644.
McCormick et al. "Genetically engineered Tobacco mosaic virus as nanoparticle vaccines", Expert Rev Vaccines, 2008, 7(1):33-41.
McCormick, et al. "TMV-peptide fusion vaccines induce cell-mediated immune responses and tumor protection in two murine models", Vaccine 24 (2006) 6414-6423.
Okada, "Historical overview of research on the tobacco mosaic virus genome: genome organization, infectivity and gene manipulation", Phil. Trans. Soc. Lond B., 1999, 354: 569-582.
Palmer, et al. "Protection of rabbits against cutaneous papillomavirus infection using recombinant tobacco mosaic virus containing L2 capsid epitopes", Vaccine 24 (2006) 5516-5525.
Pereira,et al. "Antigenic structure of the coat protein of potato mop-top furovirus", Virology, 1994, 203(2): 277-285.
Peterson, et al. "Electron microscopy of soil-borne wheat mosaic virus in host cells", Virology, 1970, 42(2): 304-310.
Petukhova, et al. 2011, vol. 278, No. Suppl. 1, Iss. pp. 161, In the meeting of 36th FEBS Congress of the Biochemistry for tomorrows Medicine. Torino, Italy.
Shirako, et al. "Similarity and Divergence among Viruses in the Genus Furovirus", Virology, 2000, 270(1): 201-207.
Smith, et al., "Display of Peptides on the Surface of Tobacco Mosaic Virus Particles", Current Topics in Microbiology and Immunology, 332, Springer-Verlag Berlin Heidelberg 2009, pp. 13-31.

(Continued)

*Primary Examiner* — Bao Q Li
(74) *Attorney, Agent, or Firm* — James S. Keddie; Bozicevic, Field & Francis LLP

(57) ABSTRACT

Provided herein is a recombinant rod-shaped viral particle comprising a fusion protein comprising a coat protein for a rod-shaped plant virus and a epitope from a human and/or human pathogen, where the epitope is disposed on the outer surface of the viral particle. In certain cases, the amino acid sequence of the coat protein is at least 40% identical to the amino acid sequence of the Tobacco Mosaic Virus (TMV) coat protein.

10 Claims, 9 Drawing Sheets

Specification includes a Sequence Listing.

(56) References Cited

OTHER PUBLICATIONS

Smith, et al. "Modified Tobacco mosaic virus particles as scaffolds for display of protein antigens for vaccine applications", Virology 348 (2006) 475-488.
Staczek, et al. "Immunization with a chimeric tobacco mosaic virus containing an epitope of outer membrane protein F of Pseudomonas aeruginosa provides protection against challenge with P. aeruginosa", Vaccine, vol. 18, Issue 21, Apr. 2000, pp. 2266-2274.
Steven, et al. "The molecular organization of beet necrotic yellow vein virus", Virology, 1981, 113(2): 428-438.
Werner, et al., "Immunoabsorbent nanoparticles based on a tobamovirus displaying protein A", PNAS, 2006, 103 (47): 17678-17683.
Wu, et al., "Expression of foot-an-mouth disease virus epitopes in tobacco by a tobacco mosaic virus-based vector", Vaccine, 2003, 21: 4390-4398.
Zharikova, et al., "Influenza Type A Virus Escape Mutants Emerge In Vivo in the Presence of Antibodies to the Ectodomain of Matrix Protein 2", Journal of Virology, 2005, 79(11): 6644-6654.

SEQUENCE LISTING

<160> NUMBER OF SEQ ID NOS: 21

<210> SEQ ID NO 1
<211> LENGTH: 23
<212> TYPE: PRT
<213> ORGANISM: Artificial Sequence
<220> FEATURE:
<223> OTHER INFORMATION: Synthetic peptide

<400> SEQUENCE: 1

```
Ser Leu Leu Thr Glu Val Glu Thr Pro Ile Arg Asn Glu Trp Gly Cys
1               5                   10                  15

Arg Cys Asn Asp Ser Ser Asp
            20
```

<210> SEQ ID NO 2
<211> LENGTH: 23
<212> TYPE: PRT
<213> ORGANISM: Artificial Sequence
<220> FEATURE:
<223> OTHER INFORMATION: Synthetic peptide

<400> SEQUENCE: 2

```
Ser Leu Leu Thr Glu Val Glu Thr Pro Ile Arg Asn Glu Trp Gly Ser
1               5                   10                  15

Arg Ser Asn Asp Ser Ser Asp
            20
```

<210> SEQ ID NO 3
<211> LENGTH: 23
<212> TYPE: PRT
<213> ORGANISM: Artificial Sequence
<220> FEATURE:
<223> OTHER INFORMATION: Synthetic peptide

<400> SEQUENCE: 3

```
Ser Leu Leu Thr Glu Val Glu Thr Pro Ile Arg Asn Glu Trp Gly Ala
1               5                   10                  15

Arg Ala Asn Asp Ser Ser Asp
            20
```

<210> SEQ ID NO 4
<211> LENGTH: 69
<212> TYPE: DNA
<213> ORGANISM: Artificial Sequence
<220> FEATURE:
<223> OTHER INFORMATION: Synthetic polynucleotide

<400> SEQUENCE: 4

```
tcactcttga cagaggtgga aacaccaatc agaaacgagt ggggatgcag atgcaacgac     60

tcatccgac                                                             69
```

<210> SEQ ID NO 5
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 5

```
tcactcttga cagaggtgga aacaccaatc agaaacgagt ggg                       43
```

<210> SEQ ID NO 6
<211> LENGTH: 43

<212> TYPE: DNA
<213> ORGANISM: Artificial Sequence
<220> FEATURE:
<223> OTHER INFORMATION: Synthetic polynucleotide

<400> SEQUENCE: 6
gtcggatgag tcgttgcatc tgcatcccca ctcgtttctg att 43

<210> SEQ ID NO 7
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 7
ctgaggatcc tcactcttga cagaggtgga aac 33

<210> SEQ ID NO 8
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 8
ctgaaagctt gtcggatgag tcgttgcatc t 31

<210> SEQ ID NO 9
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 9
cttctggttt ggtttggacc tcttcactct tgacagaggt ggaaac 46

<210> SEQ ID NO 10
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 10
gactacctca agttgcagga ccgtcggatg agtcgttgca tctgc 45

<210> SEQ ID NO 11
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 11
ctcaagttgc aggaccgtcg gatgagtcgt tagatcttga tc 42

<210> SEQ ID NO 12
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 12

-continued tgagtcgttt gctctagctc ccca 24

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
agaggtccaa accaaaccag 20

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
ggtcctgcaa cttgaggtag 20

<210> SEQ ID NO 15
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 15
ggagggccca tggaac 16

<210> SEQ ID NO 16
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 16
gtgaattcga tctagtaaca tagatgacac c 31

<210> SEQ ID NO 17
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 17
gggaaaaata gtagtaatga tcggtcagtg ccgaacaaga ac 42

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
tgggccccta ccgggggtaa 20

<210> SEQ ID NO 19
<211> LENGTH: 23
<212> TYPE: PRT
<213> ORGANISM: Artificial Sequence -continued

```
<220> FEATURE:
<223> OTHER INFORMATION: Synthetic peptide

<400> SEQUENCE: 19

Ser Leu Leu Thr Glu Val Glu Thr Pro Ile Arg Asn Glu Trp Gly Cys
1               5                   10                  15

Arg Cys Asn Gly Ser Ser Asp
            20


<210> SEQ ID NO 20
<211> LENGTH: 23
<212> TYPE: PRT
<213> ORGANISM: Artificial Sequence
<220> FEATURE:
<223> OTHER INFORMATION: Synthetic peptide

<400> SEQUENCE: 20

Ser Leu Leu Thr Glu Val Glu Thr Pro Thr Arg Ser Glu Trp Glu Cys
1               5                   10                  15

Arg Cys Ser Asp Ser Ser Asp
            20


<210> SEQ ID NO 21
<211> LENGTH: 159
<212> TYPE: PRT
<213> ORGANISM: Nicotiana benthamiana

<400> SEQUENCE: 21

Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Glu Val Trp Lys Pro Ser Pro Gln Val Thr Val Arg Phe Pro
    50                  55                  60

Asp Ser Asp Phe Lys Val Tyr Arg Tyr Asn Ala Val Leu Asp Pro Leu
65                  70                  75                  80

Val Thr Ala Leu Leu Gly Ala Phe Asp Thr Arg Asn Arg Ile Ile Glu
                85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
        115                 120                 125

Leu Ile Val Glu Leu Ile Arg Gly Thr Gly Ser Tyr Asn Arg Ser Ser
    130                 135                 140

Phe Glu Ser Ser Ser Gly Leu Val Trp Thr Ser Gly Pro Ala Thr
145                 150                 155
```

PRODUCTION OF AN IMMUNOGEN USING A PLANT VIRUS

CROSS-REFERENCING

This application is a continuation-in-part of application Ser. No. 14/429,264, filed on Mar. 18, 2015, which application is a § 371 filing of PCT/US2013/068486, filed on Nov. 5, 2013, which application claims the benefit of provisional application Ser. No. 61/723,704, filed on Nov. 7, 2012, which applications are incorporated by reference herein.

INTRODUCTION

There is currently an ongoing need for the development of new vaccine strategies to combat influenza virus and other human and animal infectious diseases.

SUMMARY

Some aspects of this disclosure relate to a recombinant rod-shaped viral particle comprising a fusion protein comprising: (i) a coat protein for a rod-shaped plant virus and (ii) an epitope from a human and/or animal pathogen; wherein the epitope is disposed on the outer surface of the viral particle.

The plant virus may be any rod-shaped virus. However, in certain embodiments, the amino acid sequence of the coat protein may be at least 40% identical to the amino acid sequence of a wild type Tobacco Mosaic Virus (TMV) coat protein.

The epitope may be any immunologically relevant epitope and in certain cases the amino acid sequence of the epitope has a wild type amino acid sequence except for a substitution of any cysteine, serine and/or threonine residues by neutral, non-polar amino acids with aliphatic side chains (such as glycine, valine, leucine, isoleucine, or alanine). In some cases, the epitope has an amino acid sequence that is at least 60% identical to the amino acid sequence of the influenza A virus M2e epitope of SEQ ID NO:1. For example, the epitope may have an amino acid sequence that is at least 60% identical to the influenza A virus M2e epitope of SEQ ID NO:1, except for serine and/or neutral, non-polar with aliphatic side chains at positions corresponding to cys17 and cys19 of SEQ ID NO:1 and/or any serine and/or threonine residues of SEQ ID NO:1. The amino acids with an aliphatic side chains may be glycine, valine, leucine, isoleucine, or alanine.

The epitope may be inserted at any position in the plant viral coat protein, e.g., within 30 amino acids of the C-terminus, within 30 amino acids of the N-terminus, or centrally (i.e., not within 30 amino acids of the C- or N-termini), as long as the epitope is presented on the exterior surface of the particle. Because the structures of many rod-shaped particles are known, the site of insertion of the epitope can be readily discerned.

In certain cases, the epitope is inserted into the plant viral coat protein within 5 amino acids of the position defined by the junction between Ser155 and Gly156 of the TMV coat protein, or a corresponding position in a non-TMV coat protein. In particular cases, up to 10 amino acids may be deleted from the site of insertion. In particular cases, the epitope may inserted into the plant viral coat protein between Ser155 and Gly156 of the TMV coat protein, or a corresponding position in a non-TMV coat protein.

The particle may have been made by plant cells, e.g., a plant that is transgenic or has been transiently transfected, explants that have been transfected, or plant cells grown in culture. The particles can be isolated from the plant cells by any suitable method.

Some aspects of this disclosure relate to a method of producing an immune response in an animal, e.g. a mammal such as a human, rabbit, mouse, or a non-human primate. In certain embodiments, this method comprises administering a subject recombinant rod-shaped viral particle to an animal, thereby causing the animal to produce antibodies that recognize the epitope. In some cases, the administering protects the animal against future infection by the pathogen, i.e., vaccinates the animal against the pathogen.

In some embodiments, the viral particle can administered to the animal in conjunction with an adjuvant, and the administering can be done parenterally, enterally or orally.

Other aspects of this disclosure relate to an immunogenic fusion protein. In some embodiments the fusion protein comprises: a fusion partner; and the influenza A virus M2e epitope, the influenza A virus M2e epitope, wherein the influenza A virus M2e epitope is at least 60% identical to the amino acid sequence of the influenza A virus M2e epitope of SEQ ID NO:1, except that amino acids corresponding to cys17 and cys19 of SEQ ID NO:1 are substituted by serine and/or neutral, non-polar amino acids with aliphatic side chains, and/or any serine or threonine residues are substituted by neutral, non-polar amino acids with aliphatic side chains. In particular cases, the amino acids with an aliphatic side chain are glycine, valine, leucine, isoleucine, or alanine residues. In certain embodiments, the fusion partner can be a viral coat protein, e.g., coat protein for a rod-shaped virus. In other embodiments, the disclosure provides a method in which an antigen can be made more immunogenic by substituting any cysteine, serine or threonine residues by neutral, non-polar amino acids with aliphatic side chains, and then expressing it using expression system described herein A polynucleotide encoding the fusion protein is also provided, as is a vector containing the same. A cell comprising the vector is also provided.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
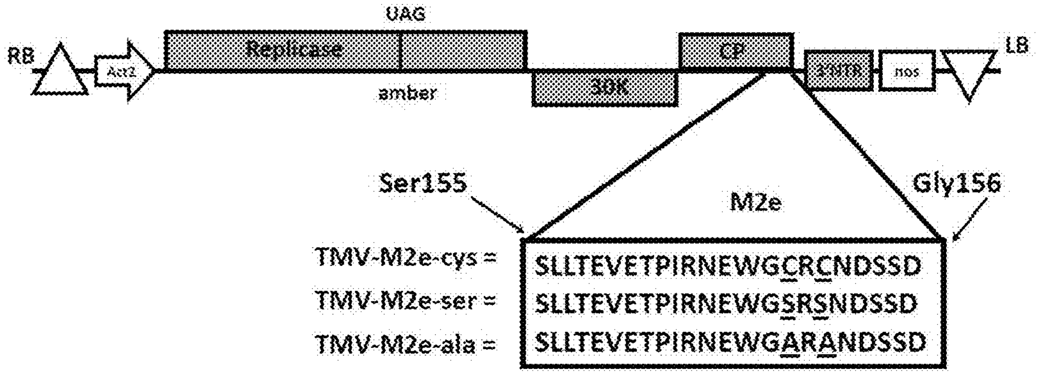
FIG. 1 shows a schematic representation of TMV-based viral vectors. Shaded boxes correspond to the replicase, 30 kDa movement protein, coat protein (CP) gene and the 3'-nontranslated region (3'-NTR) of TMV-U1 genome. RB, LB—right and left T-DNA borders, respectively. Act 2-Actin2 transcriptional promoter from *Arabidopsis thaliana*; nos—terminator of transcription from the nopaline synthase gene. Boxed sequences show the three M2e versions inserted between residues 155 and 156 of the CP Amino acid substitutions in M2e sequence are underlined. From top to bottom SEQ ID NOS. 1-3.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms “a”, “and”, and “the” include plural referents unless the context clearly dictates otherwise. Thus, for example, reference to “a protease” includes a plurality of such proteases and reference to “the protease cleavage site” includes reference to one or more protease cleavage sites and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms “polypeptide” and “protein”, used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A "deletion" is defined as a change in either amino acid or nucleotide sequence in which one or more amino acid or nucleotide residues, respectively, are absent as compared to an amino acid sequence or nucleotide sequence of a naturally occurring polypeptide. In the context of a polypeptide or polynucleotide sequence, a deletion can involve deletion of about 2, about 5, about 10, up to about 20, up to about 30 or up to about 50 or more residues.

An "insertion" or "addition" is a change in an amino acid or nucleotide sequence which has resulted in the addition of one or more amino acid or nucleotide residues. An insertion or addition of up to about 10, up to about 20, up to about 30 or up to about 50 or more amino acids.

A "substitution" results from the replacement of one or more amino acids or nucleotides by different amino acids or nucleotides, respectively. It is understood that a polypeptide may have conservative amino acid substitutions which have substantially no effect on activity. By conservative substitutions is intended combinations such as gly, ala; val, ile, leu; asp, glu; asn, gln; ser, thr; lys, arg; and phe, tyr.

The term "biologically active" refers to a polypeptide having structural and biochemical functions of a naturally occurring polypeptide.

As used herein, the terms "determining," "measuring," "assessing," and "assaying" are used interchangeably and include both quantitative and qualitative determinations.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, preferably 75% free, and most preferably 90% free from other components with which it is naturally associated.

A "coding sequence" or a sequence that "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Operably linked" refers to an arrangement of elements wherein the components so described are configured so as to perform their usual function. Thus, in the case of a promoter, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" comprises any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into target cells. Thus, the term includes cloning and expression vehicles, as well as viral vectors.

A first polynucleotide is "derived from" a second polynucleotide if it has the same or substantially the same nucleotide sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

The term "unit dosage form" as used herein refers to physically discrete units suitable as unitary dosages for subjects (e.g., animals, usually humans), each unit containing a predetermined quantity of an agent, e.g. a vaccine in an amount sufficient to produce the desired effect in association with a pharmaceutically acceptable diluent, carrier or vehicle. The specifications for the novel unit dosage forms of the present invention will depend on a variety of factors including, but not necessarily limited to, the particular agent employed and the effect to be achieved, and the pharmacodynamics associated with each compound in the host.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of modified pro-polypeptide-enciding nucleic acids that can provide for enhanced or desirable effects in the subject (e.g., reduction of pathogen load, increase in CD4 count, reduction of disease symptoms, etc.).

"Subject", "host" and "patient" are used interchangeably herein, to refer to an animal, human or non-human, susceptible to or having an infection by an pathogen and amenable to therapy according to the methods of the invention. Generally, the subject is a mammalian subject. Exemplary subjects include, but are not necessarily limited to, humans, cattle, sheep, goats, pigs, dogs, cats, and horses, with humans being of particular interest.

As used herein, the term "antigenic compound" refers to any substance that can be recognized by the immune system (e.g., bound by an antibody or processed so as to elicit a cellular immune response) under appropriate conditions.

An "antigen" as used herein includes but is not limited to cells; cell extracts; proteins; lipoproteins; glycoproteins; nucleoproteins; polypeptides; peptides; polysaccharides; polysaccharide conjugates; peptide mimics of polysaccharides; lipids; glycolipids; carbohydrates; viruses; viral extracts; bacteria; bacterial extracts; fungi; fungal extracts; multicellular organisms such as parasites; and allergens. In some embodiments of the invention the antigen is a polypeptide, e.g. a native polypeptide; a polypeptide produced by recombinant methods, included in vitro cell free synthesis, bacterial and prokaryotic expression systems; and the like. Such antigens include, without limitation, viral antigens derived from HIV; influenza, smallpox (vaccinia), measles, mumps, rubella, poliovirus, rotavirus, varicella (chickenpox), hepatitis A, B, C, D virus, bacterial antigens, tumor antigens, and the like. Bacterial antigens of interest include, without limitation, antigens derived from *Bacillus anthracia; Bordetella pertussis, Clostridium tetani, Haemophilus Influenzae, Corynebacterium diphtherias, Meningococcus* sp., *Streptococcus pneumoniae, Salmonella typhi, Mycobacterium tuberculosis*, etc.

Antigens may be exogenous (e.g., from a source other than the individual to whom the antigen is administered, e.g., from a different species) or endogenous (e.g., originating from within the host, e.g., a diseased element of body, a cancer antigen, a virus infected cell producing antigen, and the like). Antigens may be native (e.g., naturally-occurring); synthetic; or recombinant Antigens include crude extracts; whole cells; and purified antigens, where "purified" indicates that the antigen is in a form that is enriched relative to the environment in which the antigen normally occurs and/or relative to the crude extract, for example, a cultured form of the antigen.

An "immunogenic composition" as used here in refers to a composition that causes an immune response when administered to a host.

An "effective amount of an antigenic compound" refers to an amount of antigenic compound which, in optional combination with an adjuvant, will cause the subject to produce a specific immunological response to the antigenic compound.

The term "immune response" refers to any response to an antigenic or immunogenic compound by the immune system of a vertebrate subject. Exemplary immune responses include, but are not limited to local and systemic cellular as well as humoral immunity, such as cytotoxic T lymphocytes (CTL) responses, including antigen-specific induction of $CD8^+$ CTLs, helper T-cell responses including T-cell proliferative responses and cytokine release, and B-cell responses including antibody response.

The term "eliciting an immune response" is used herein generally to encompass induction and/or potentiation of an immune response.

The term "inducing an immune response" refers to an immune response that is stimulated or initiated.

The term "potentiating an immune response" refers to a pre-existing immune response that is improved, furthered, supplemented, amplified, enhanced, increased or prolonged.

The expression "enhanced immune response" or similar means that the immune response is elevated, improved or enhanced to the benefit of the host relative to the prior immune response status, for example, before the administration of an immunogenic composition of the invention.

The terms "humoral immunity" and "humoral immune response" refer to the form of immunity in which antibody molecules are produced in response to antigenic stimulation.

The terms "cell-mediated immunity" and "cell-mediated immune response" are meant to refer to the immunological defense provided by lymphocytes, such as that defense provided by T cell lymphocytes when they come into close proximity to their victim cells. A cell-mediated immune response normally includes lymphocyte proliferation. When "lymphocyte proliferation" is measured, the ability of lymphocytes to proliferate in response to a specific antigen is measured. Lymphocyte proliferation is meant to refer to B cell, T-helper cell or cytotoxic T-lymphocyte (CTL) cell proliferation.

The term "immunogenic amount" refers to an amount of antigenic compound sufficient to stimulate an immune response, when administered with a subject immunogenic composition, as compared with the immune response elicited by the antigen in the absence of immunogenic composition.

The term "immunopotentiating amount" refers to the amount of an immunogenic composition needed to effect an increase in antibody titer and/or cell-mediated immunity when administered with an immunogenic composition, as compared with the increase in antibody and/or cell mediated immunity level observed in the absence of the immunogenic composition.

A "rod-shaped" virus is as virus that has a rod-shaped virion, as described in Robinson et al. (Plant Viruses with Rod-shaped Virions Wiley Online Library, 2006) and Van Regenmortel et al. (The Plant Viruses: The rod-shaped plant viruses Plenum Press, 1986—424 pages).

A "fusion protein" is a polypeptide containing at least two amino acid sequences that are not found together in nature.

The "outer surface" of a particle is the surface of a particle that is exposed to the exterior.

DESCRIPTION OF EXEMPLARY EMBODIMENTS

Some embodiments provide recombinant plant viruses that express fusion proteins that are formed by fusions between a plant viral coat protein and an epitope. By infecting plant cells with a subject recombinant plant virus of the invention, relatively large quantities of the epitope may be produced in the form of a fusion protein. The fusion protein encoded by the recombinant plant virus may have any of a variety of forms. The epitope may be fused to the amino terminus of the viral coat protein or the epitope may be fused to the carboxyl terminus of the viral coat protein. In other embodiments of the invention, the epitope may be fused internally to a coat protein. The fusion protein may be used as an antigen for antibody development or to induce a protective immune response.

This disclosure also provides recombinant plant viruses that code for the expression of a fusion between a plant viral coat protein and epitope. Such recombinant plant viruses can provide for systemic expression of the fusion protein, by systemically infecting cells in a plant. Thus by employing the subject recombinant plant viruses, large quantities of a fusion protein may be produced.

A fusion protein may comprise two portions: (i) a plant viral coat protein and (ii) an epitope. The plant viral coat protein portion may be derived from the same plant viral coat protein that serves a coat protein for the virus from which the genome of the expression vector is primarily derived, i.e., the coat protein is native with respect to the recombinant viral genome. Alternatively, the coat protein portion of the fusion protein may be heterologous, i.e., non-native, with respect to the recombinant viral genome. In some embodiments, the 17.5 kDa coat protein of tobacco mosaic virus is used in conjunction with a tobacco mosaic virus derived vector. The epitope portion of the fusion protein may consist of any immunologically relevant sequence, and may be at least 10 amino acids in length, e.g., at least 20 amino acids, at least 30 amino acids, up to 100 amino acids or more in length. In one embodiment, the epitope portion of the fusion protein may in the range of 10 to 30 amino acids in length.

The fusion protein, or a portion thereof, may be injected into a mammal, along with suitable adjuvants, so as to produce an immune response directed against the epitope portion of the fusion protein. The immune response against the epitope portion of the fusion protein has numerous uses, such uses include, protection against infection, and the generation of antibodies useful in immunoassays.

The location (or locations) in the fusion protein of the invention where the viral coat protein portion is joined to the epitope is referred to herein as the fusion junction. A given fusion protein may have one or more fusion junctions. The fusion junction may be located at the carboxyl terminus of the coat protein portion of the fusion protein (joined at the amino terminus of the epitope portion). The fusion junction may be located at the amino terminus of the coat protein portion of the fusion protein (joined to the carboxyl terminus of the epitope). In other embodiments of the invention, the fusion protein may have two fusion junctions. In those fusion proteins having two fusion junctions, the epitope may be located internal with respect to the carboxyl and amino terminal amino acid residues of the coat protein portion of the fusion protein, i.e., an internal fusion protein. Internal fusion proteins may comprise an entire plant virus coat protein amino acid residue sequence (or a portion thereof) that is "interrupted" by the epitope, i.e., the amino terminal segment of the coat protein portion is joined at a fusion junction to the amino terminal amino acid residue of the epitope and the carboxyl terminal segment of the coat protein is joined at a fusion junction to the carboxyl terminal amino acid residue of the epitope.

When the fusion is an internal fusion, the fusion junction may be located at a variety of sites within a coat protein. Suitable sites for the fusion junctions may be determined either through routine systematic variation of the fusion junction locations so as to obtain an internal fusion protein with the desired properties. Suitable sites for the fusion junction may also be determined by analysis of the three dimensional structure of the coat protein so as to determine sites for insertion of the epitope so that the epitope is presented on the exterior surface of the particle. Detailed three dimensional structures of plant viral coat proteins and their orientation in the virus have been determined and are publicly available to a person of ordinary skill in the art. Detailed structural information on the virus and coat protein of Tobacco Mosaic Virus can be found, among other places in Namba et al. (J. Mol. Biol. 1989 208:307-325) and Pattanayek and Stubbs (J. Mol. Biol. 1992 228:516-528). Knowledge of the three dimensional structure of a plant virus particle and the assembly process of the virus particle permits the person of ordinary skill in the art to design various coat protein fusions of the invention, including insertions, and partial substitutions. For example, if the epitope is of a hydrophilic nature, it may be appropriate to fuse the peptide to the TMV CP (Tobacco mosaic tobamovirus coat protein) region known to be oriented as a surface loop region. Likewise, alpha helical segments that maintain subunit contacts might be substituted for appropriate regions of the TMV CP helices or nucleic acid binding domains expressed in the region of the TMV CP oriented towards the genome. The amino acid sequence of one example of a TMV protein is provided by NCBI Reference Sequence: NC_001367.1 (GI:9626125), which is incorporated by reference herein.

The amino acid sequence of the coat protein may be at least 40% identical to (e.g., at least 50% identical to, at least 60% identical to, at least 70% identical to, at least 80% identical to, at least 90% identical to, at least 95% identical to or at least 98% identical to) the coat protein of any rod-shaped virus, including, but not limited to, a tobamovirus (e.g., TMV), a tobravirus, a hordeivirus, a furovirus, a benyvirus, a pomovirus, or a pecluvirus. Likewise, the amino acid sequence of the epitope may be at least 60% identical to (e.g., at least 70% identical to, at least 80% identical to, at least 90% identical to at least 95% identical to or at least 98% identical to) the amino acid sequence of a wild type epitope, e.g., the influenza A virus M2e epitope, or the same epitope in a different strain, e.g., H1N1, H2N2, H3N2, H5N1, H7N7, H1N2 H9N2, H7N2 or H10N7. Suitable insertion sites in non-TMV coat proteins can be determined using the structure of the TMV virion. For example, the epitope is inserted into the plant viral coat protein within 5 amino acids (e.g., within 4 amino acids, within 3 amino acids, within 2 amino acids or within 1 amino acid) of the position defined by the junction between Ser155 and Gly156 of the TMV coat protein, or a corresponding position in a non-TMV coat protein, where a corresponding position in a non-TMV coat protein is one that is at an equivalent position to the position in TMV.

In certain embodiment, the fusion junctions on the subject fusion proteins may be designed so as to comprise an amino acid sequence that is a substrate for protease. By providing a coat fusion protein having such a fusion junction, the epitope may be conveniently cleaved from the coat protein fusion by using a suitable proteolytic enzyme. The proteolytic enzyme may contact the fusion protein either in vitro or in vivo.

The expression of a subject fusion protein may be driven by any of a variety of promoters functional in the genome of the recombinant plant viral vector. In one embodiment, a subject fusion protein is expressed from plant viral subgenomic promoters using vectors as described in U.S. Pat. No. 5,316,931.

In addition to providing the described viral coat fusion proteins, also provided are virus particles that comprise the subject fusion protein. The coat of such virus particles may consist entirely of coat fusion protein. In another embodiment, the virus particle coat may consist of a mixture of coat fusion proteins and non-fusion coat protein, wherein the ratio of the two proteins may be varied.

Recombinant plant cells comprising the subject coat fusion proteins and/or virus particles comprising the subject coat fusion proteins are also provided. These plant cells may be produced either by infecting plant cells (either in culture or in whole plants) with infectious virus or with polynucleotides encoding the genomes of the infectious virus particle. In one embodiment, the plant may be a *Nicotiana benthamiana* plant.

The subject fusion protein may be used to produce a vaccine. In some embodiments, the fusion protein may vaccinate against human papillomavirus (HPV) (which are implicated in the etiology of cervical cancer, and other neoplasias, including but not limited to HPV-16, HPV-18, HPV-31, HPV-33, HPV-35 and HPV-52, HPV-6 and HPV-11), hemorrhagic fever-causing viruses such as Rift Valley fever virus (RVFV) and Ebola viruse (EBOV), as these pathogens present significant threat to the US population if weaponized by terrorists. In addition, it is of interest to provide vaccines against human immunodeficiency virus type 1 (HIV-1), and against parvoviruses that are significant pathogens of human companion animals (particularly cats and dogs), and livestock (especially pigs). Other pathogens include avian influenza, foot-and-mouth disease.

In some embodiments, the epitope is from an infectious agent, including protozoan, bacterial, fungal (including unicellular and multicellular), and viral infectious agents. Examples of suitable viral antigens are described herein and are known in the art. Bacteria include *Hemophilus influenza, Mycobacterium tuberculosis* and *Bordetella pertussis*. Protozoan infectious agents include malarial plasmodia, *Leishmania* species, *Trypanosoma* species and *Schistosoma* species. Fungi include *Candida albicans*.

In some embodiments, the epitope is a viral antigen. Viral polypeptide antigens include, but are not limited to, core proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein. References discussing influenza vaccination include Scherle and Gerhard (1988) Proc. Natl. Acad. Sci. USA 85:4446-4450; Scherle and Gerhard (1986) J. Exp. Med. 164:1114-1128; Granoff et al. (1993) Vaccine 11:S46-51; Kodihalli et al. (1997) J. Virol. 71:3391-3396; Ahmeida et al. (1993) Vaccine 11:1302-1309; Chen et al. (1999) Vaccine 17:653-659; Govorkova and Smirnov (1997) Acta Virol. (1997) 41:251-257; Koide et al. (1995) Vaccine 13:3-5; Mbawuike et al. (1994) Vaccine 12:1340-1348; Tamura et al. (1994) Vaccine 12:310-316; Tamura et al. (1992) Eur. J. Immunol. 22:477-481; Hirabayashi et al. (1990) Vaccine 8:595-599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

Many antigenic peptides and proteins are known, and available in the art; others can be identified using conventional techniques. For immunization against tumor formation, immunomodulatory peptides can include tumor cells (live or irradiated), tumor cell extracts, or protein subunits of tumor antigens such as Her-2/neu, Mara, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including epitopes from sperm proteins in the fusion protein. Lea et al. (1996) Biochim Biophys. Acta 1307:263.

Optionally the epitope may be joined to the coat protein at one or both of the amino terminus and carboxy terminus using a short flexible linker, e.g. comprising at least about 2, 3, 4 or more glycine, serine and/or alanine residues. One such linker comprises the motif (GGGGS), and may be present in one or more copies.

As noted above, an immunogenic fusion protein comprising a fusion partner; and the influenza A virus M2e epitope, wherein the influenza A virus M2e epitope is at least 60% identical to the amino acid sequence of the influenza A virus M2e epitope of SEQ ID NO:1, except that amino acids corresponding to cys17 and cys19 of SEQ ID NO:1, and any serine and/or threonine residues neutral, non-polar amino acids with an aliphatic side chains. In certain cases, the fusion protein may also contain a viral coat protein, as described above. In other embodiments, the M2e epitope may be presented as an antigen by another protein, e.g., a coat protein for a non-rod-shaped virus or another antigen presentation protein.

The subject particles are useful for administering to an individual in need of immune stimulation (in the context of, for example, infectious disease, cancer, and allergy) and generally comprise any of the polypeptide populations described herein in a sufficient amount to modulate an immune response.

The particles may be administered in a composition that also comprises a pharmaceutically acceptable excipient, and may be in various formulations. As is well known in the art, a pharmaceutically acceptable excipient is a relatively inert substance that facilitates administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington's Pharmaceutical Sciences 19th Ed. Mack Publishing (1995).

Other formulations include suitable delivery forms known in the art including, but not limited to, carriers such as liposomes. Mahato et al. (1997) Pharm. Res. 14:853-859. Liposomal preparations include, but are not limited to, cytofectins, multilamellar vesicles and unilamellar vesicles.

Generally, these compositions are formulated for administration by injection, inhalation or oral, e.g., intraperitoneally, intravenously, subcutaneously, intramuscularly, etc.

Accordingly, these compositions are preferably combined with pharmaceutically acceptable vehicles such as saline, Ringer's solution, dextrose solution, and the like. The particular dosage regimen, i.e., dose, timing and repetition, will depend on the particular individual and that individual's medical history.

In some embodiments, more than one antigen(s) may be present in a composition. Such compositions may contain at least one, at least two, at least three, at least four, at least five, or more different antigen(s). Such "cocktails", as they are often denoted in the art, may be particularly useful in immunizing against pathogens present in different variants, e.g. HIV, rotavirus, influenza, etc.

Generally, the efficacy of administering any of these compositions is adjusted by measuring any change in the immune response as described herein, or other clinical parameters.

In some embodiments, an immunogenic composition may comprise a polypeptide as described herein and an adjuvant whereby the polypeptide(s)/adjuvant are co-administered. The immunogenic composition may contain an amount of an adjuvant sufficient to potentiate the immune response to the immunogen. Adjuvants are known in the art and include, but are not limited to, oil-in-water emulsions, water-in oil emulsions, alum (aluminum salts), liposomes and microparticles including but not limited to, polystyrene, starch, polyphosphazene and polylactide/polyglycosides. Other suitable adjuvants also include, but are not limited to, MF59, DETOX™ (Ribi), squalene mixtures (SAF-1), muramyl peptide, saponin derivatives, *mycobacterium* cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) Nature 344:873-875, as well as, lipid-based adjuvants and others described herein. For veterinary use and for production of antibodies in animals, mitogenic components of Freund's adjuvant (both complete and incomplete) can be used.

In some embodiments, the particles described herein can be administered in conjunction with one or more immunomodulatory facilitators. Thus, the invention provides compositions comprising a viral particle and an immunomodulatory facilitator. As used herein, the term "immunomodulatory facilitator" refers to molecules which support and/or enhance the immunomodulatory activity of viral particle. Examples of immunomodulatory facilitators can include co-stimulatory molecules, such as cytokines, and/or adjuvants. Immunomodulatory facilitators include, but are not limited to, co-stimulatory molecules (such as cytokines, chemokines, targeting protein ligand, trans-activating factors, peptides, and peptides comprising a modified amino acid) and adjuvants (such as alum, lipid emulsions, and polylactide/polyglycolide microparticles).

The immunomodulatory particles composition can be administered in combination with other pharmaceutical and/or immunogenic and/or immunostimulatory agents and can be combined with a physiologically acceptable carrier thereof.

As with all immunogenic compositions, the immunologically effective amounts and method of administration of the particular formulation can vary based on the individual, what condition is to be treated and other factors evident to one skilled in the art. Factors to be considered include the antigenicity, whether or not the immunomodulatory particles will be complexed with or covalently attached to an adjuvant or delivery molecule, route of administration and the number of immunizing doses to be administered. Such factors are known in the art and it is well within the skill in immunology to make such determinations without undue experimentation. A suitable dosage range is one that provides the desired modulation of immune response to the antigen. Generally, a dosage range of the immunomodulatory particles may be, for example, from about any of the following: 0.01 to 100 μg, 0.01 to 50 μg, 0.01 to 25 μg, 0.01 to 10 μg, 1 to 500 μg, 100 to 400 μg, 200 to 300 μg, 1 to 100 μg, 100 to 200 μg, 300 to 400 μg, 400 to 500 μg. Alternatively, the doses can be about any of the following: 0.1 μg, 0.25 μg, 0.5 μg, 1.0 μg, 2.0 μg, 5.0 μg, 10 μg, 25 μg, 50 μg, 75 μg, 100 μg. Accordingly, dose ranges can be those with a lower limit about any of the following: 0.1 μg, 0.25 μg, 0.5 μg and 1.0 μg; and with an upper limit of about any of the following: 250 μg, 500 μg and 1000 μg. The absolute amount given to each patient depends on pharmacological properties such as bioavailability, clearance rate and route of administration.

The effective amount and method of administration of the particular formulation can vary based on the individual patient and the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. The absolute amount given to each patient depends on pharmacological properties such as bioavailability, clearance rate and route of administration.

Parenteral routes of administration include but are not limited to electrical (iontophoresis) or direct injection such as direct injection into a central venous line, intravenous, intramuscular, intraperitoneal, intradermal, or subcutaneous injection. Compositions suitable for parenteral administration include, but are not limited, to pharmaceutically acceptable sterile isotonic solutions. Such solutions include, but are not limited to, saline and phosphate buffered saline for injection of the immonogenic composition.

Naso-pharyngeal and pulmonary routes of administration include, but are not limited to, inhalation, transbronchial and transalveolar routes. Embodiments includes immunogenic compositions suitable for administration by inhalation including, but not limited to, various types of aerosols for inhalation, as well as powder forms for delivery systems. Devices suitable for administration by inhalation of immunogenic compositions include, but are not limited to, atomizers and vaporizers. Atomizers and vaporizers filled with the powders are among a variety of devices suitable for use in inhalation delivery of powders.

The methods of producing suitable devices for injection, topical application, atomizers and vaporizers are known in the art and will not be described in detail.

Analysis (both qualitative and quantitative) of the immune response to the immunomodulatory particles can be by any method known in the art, including, but not limited to, measuring antigen-specific antibody production (including measuring specific antibody subclasses), activation of specific populations of lymphocytes such as CD4+ T cells or NK cells, production of cytokines such as IFNγ, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Serum concentrations of cytokines can be measured, for example, by ELISA. These and other assays to evaluate the immune response to an immunogen are well known in the art. See, for example, Selected Methods in Cellular Immunology (1980) Mishell and Shiigi, eds., W. H. Freeman and Co.

In some instances, a Th1 or Th2-type response is stimulated, i.e., elicited and/or enhanced. Stimulating a Th1 or Th2-type immune response can be determined in vitro or ex vivo by measuring cytokine production from cells treated with an immunogenic composition as compared to those treated without the immunogenic composition. Methods to determine the cytokine production of cells include those methods described herein and any known in the art. The type of cytokines produced in response to treatment indicates a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, and IFN-γ. In contrast, "Th2-type biased cytokines" refers to those associated with a Th2-type immune response, and include, but are not limited to, IL-4, IL-5, and IL-13.

Further embodiments are summarized below.

Also provided herein is a method of potentiating an immune response against an antigen comprising one or more B-cell antigenic epitopes and/or one or more T-cell antigenic epitopes in an animal, said method comprising the step of administering to said animal said antigen, wherein said antigen comprising four or more amino acid residues and one or more substitutions of amino acid residues cysteine, serine and threonine to neutral non-polar aminoacids with aliphatic side chains is produced in plant, plant tissue or in a plant cell, and wherein said immune response is a humoral and/or cellular response. In particular embodiments, the antigen may produced in plants by recombinant virus comprising a polynucleotide encoding said antigen capable of being replicated in plant, plant tissue or in a plant cell, said polynucleotide further comprising a promoter functional in plants 5'-terminal to the encoding region.

Also provided are recombinant viral particles (RVP) or recombinant virus-like particles (VLP) comprising a plurality of fusion protein molecules, wherein said fusion protein comprising the following fusion protein domains: a plant viral coat protein, and a recombinant protein comprising said antigen, wherein said antigen is amino-terminal to the plant viral coat protein and/or carboxy-terminal to the plant viral coat protein and/or said fusion protein is an internal fusion protein, wherein said antigen is disposed on the outer surface of said RVP and/or VLP.

In some embodiments, the viral particles or virus-like particles according to claim 3, wherein said viral particles are rod-shaped. The viral coat protein may be the coat protein of tobacco mosaic virus or a protein having an identity of at least 40%, at least 60 or at least 80% to the coat protein of tobacco mosaic virus. In some cases, the viral particles display two or more different antigens on their surface. In one embodiment, the recombinant protein is influenza A epitope M2e or a derivative thereof.

In particular cases, the viral particles comprise at most 20% (e.g., at most 10%) of free viral coat protein, measured on a molar basis.

Also provided is a process of producing the above-described antigen by expressing said antigen in a plant, in plant tissue or in plant cells said antigen comprising four or more amino acid residues and one or more substitutions of amino acid residues cysteine, serine and threonine to neutral non-polar aminoacids with aliphatic side chains.

A process of producing said recombinant viral particles or recombinant virus-like particles as described above is also provided. This method may comprise expressing said fusion protein in a plant, in plant tissue or in plant cells, said fusion protein comprising a said antigen and said plant viral coat protein. This method may comprise introducing a polynucleotide encoding said antigen into a plant cell by *Agrobacterium*-mediated delivery and optionally isolating said viral particles from said plant cell. The viral particles may be rendered infection-deficient by chemical inactivation.

Also provided is a process of producing recombinant viral particles or recombinant virus-like particles comprising assembling recombinant viral particles in a mixture comprising fusion protein as described and a second protein being or comprising a coat protein under conditions allowing assembly of viral particles comprising said fusion protein and said second protein.

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

EXAMPLES

Aspects of the present teachings can be further understood in light of the following examples, which should not be construed as limiting the scope of the present teachings in any way.

Materials and Methods

Plasmid Constructions and Nucleotide Sequence Optimization.

The nucleotide sequence coding for the human consensus M2e-peptide (See, e.g., Liu et al, Microbes Infect. 2005; 7: 171-7; incorporated by reference for disclosure of that peptide) was optimized for the plant-based expression driven by the virus, according to codon usage in *Arabidopsis thaliana, Nicotiana tabacum* and two viral coat proteins efficiently expressed during natural infections (TMV-U1 and Alternanthera mosaic virus, AltMV-MU). In some cases, the optimization results matched each other, while in other cases, the recommendations for several codons (for example, Leu, Thr, Ile and Val) were divided and, therefore, a compromise was selected. The nucleotide sequence of the human consensus M2e epitope are shown below. Some examples of compromise codons are marked by bold font.

L (Leu)
CP TMV-U1:
tta (7); ttg (3); cta (1); ctg (1); total 12

CP AltMV-MU:
ctc (7); ttg (4); ctt (2); ctg (1); total 14

*Arabidopsis thaliana*:
ctt (24.1); ttg (20.9); ctc (16.1); tta (12.7); cta (9.9); ctg (9.8); [frequency: per thousand]

*Nicotiana tabacum*:
ctt (24.0); ttg (22.3); tta (13.4); ctc (12.3); ctg (10.2); cta (9.4); [frequency: per thousand]

T (Thr)
CP TMV-U1:
act (9); acg (3); aca (2); acc (2); total 16

CP AltMV-MU:
acc (9); aca (6); act (3); total 18

*Arabidopsis thaliana*:
act (17.5); aca (15.7); acc (10.3); acg (7.7) [frequency: per thousand]

-continued

*Nicotiana tabacum*: act (20.3); aca (17.4); acc (9.7); acg (4.5) [frequency: per thousand]

I (Ile)
CP TMV-U1:
ata (6); atc (2); att (1); total 9

CP AltMV-MU:
atc (5); att (3); ata (1); total 9

*Arabidopsis thaliana*:
att (21.5); atc (18.5); ata (12.6) [frequency: per thousand]

*Nicotiana tabacum*:
att (27.8); ata (14.0); atc (13.9) [frequency: per thousand]

V (Val)
CP TMV-U1:
gtg (4); gta (4); gtt (4); gtc (2); total 14

CP AltMV-MU:
gtg (6); gtc (4); gtt (3); total 13

*Arabidopsis thaliana*:
gtt (27.2); gtg (17.4); gtc (12.8); gta (9.9) [frequency: per thousand]

*Nicotiana tabacum*:
gtt (26.8); gtg (16.7); gta (11.4); gtc (11.1) [frequency: per thousand]

The sequence of the M2e epitope (without the methionine in the first position) is shown in the following table (SEQ ID NO:1 for the polypeptide; SEQ ID NO:4 for the polynucleotide):

| **M2e** | S | **L** | **L** | **T** | E | **V** | E | **T** | P | **I** | R | N | E | W | G | C | R | C | N | D | S | S | D |
|---|---|---|---|---|---|---|---|---|---|---|---|---|---|---|---|---|---|---|---|---|---|---|---|
| | t | **c** | **t** | **a** | g | **g** | g | **a** | c | **a** | a | a | g | t | g | t | a | t | a | g | t | t | g |
| | c | **t** | **t** | **c** | a | **t** | a | **c** | c | **t** | g | a | a | g | g | g | g | g | a | a | c | c | a |
| | a | **c** | **g** | **a** | g | **g** | a | **a** | a | **c** | a | c | g | g | a | c | a | c | c | c | a | c | c |

Cysteine to serine substitutions: ser 17-tca, ser 19-tct
Cysteine to alanine substitutions: ala 17-gct, ala 19-gca The synthetic codon-optimized M2e sequence was obtained by PCR with specific primers and then cloned into the vector pQE40 (QIAGEN, Germany) to create pQE40-M2e. All primer sequences are found in Supplemental Table 2, shown below. Subsequently, this expression construct served as a template for overlap-PCR reactions. The basic subclone pA4083 was generated from the vector pGEM5zf (Promega, USA) and contained an incomplete cDNA copy of TMV-U1 genome consisting of the 3'-terminal part of the RNA-dependent RNA polymerase (RdRp) gene, the movement protein (MP) and coat protein (CP) genes, the 3'-nontranslated region (NTR), including the tRNA-like structure, and a transcription terminator from the nopaline synthase gene (nos). The basic binary vector pTMV-5' was constructed from plasmid pBin19 and contained the 5'-terminal part (nucleotides (nt) 1-3337) of TMV-U1 RdRp gene under the control of the Actin 2 promoter from *Arabidopsis thaliana.*

The TMV U1 coat protein into which the consensus M2e-peptides were inserted as shown below, with Ser155 and Gly156 underlined:

(SEQ ID NO: 21)
MSYSITTPSQFVFLSSAWADPIELINLCTNALGNQFQTQQARTVVQRQF

SEVWKPSPQVTVRFPDSDFKVYRYNAVLDPLVTALLGAFDTRNRIIEVEN

-continued
QANPTTAETLDATRRVDDATVAIRSAINNLIVELIRGTGSYNRSSFESSSG

LVWT<u>SG</u>PAT

Supplemental Table 1
Nucleotide sequence of human consensus M2e epitope, without the methionine in the first position. Some examples of compromise codons are marked by bold font (from top to bottom SEQ ID NOS. 5-18).

| Name | Sequence 5'-3' | Coordinates in TMV U1 genome sequence (nucleotides) |
|---|---|---|
| M2e-p | tca-ctc-ttg-aca-gag-gtg-gaa-aca-cca-atc-aga-aac-gag-tgg-g | |
| M2e-m | gtc-gga-tga-gtc-gtt-gca-tct-gca-tcc-cca-ctc-gtt-tct-gat-t | |
| pQE-M2e-Bam-p | ctg-agg-atc-ctc-act-ctt-gac-aga-ggt-gga-aac | |
| pQE-M2e-Hind-m | ctg-aaa-gct-tgt-cgg-atg-agt-cgt-tgc-atc-t | |
| CP-M2e-p | ctt-ctg-gtt-tgg-ttt-gga-cct-ctt-cac-tct-tga-cag-agg-tgg-aaa-c | |

-continued

Supplemental Table 1
Nucleotide sequence of human consensus M2e epitope, without the methionine in the first position. Some examples of compromise codons are marked by bold font (from top to bottom SEQ ID NOS. 5-18).

| Name | Sequence 5'-3' | Coordinates in TMV U1 genome sequence (nucleotides) |
|---|---|---|
| CP-M2e-m | gac-tac-ctc-aag-ttg-cag-gac-cgt-cgg-atg-agt-cgt-tgc-atc-tgc | |
| CP-M2e-ser-m | ctc-aag-ttg-cag-gac-cgt-cgg-atg-agt-cgt-tag-atc-ttg-atc | |
| CP-M2e-ala-m | tga-gtc-gtt-tgc-tct-agc-tcc-cca | |
| CP-154-m | aga-ggt-cca-aac-caa-acc-ag | 6157-6176 |
| CP-155-p | ggt-cct-gca-act-tga-ggt-ag | 6177-6196 |
| Nco-mp-p | gga-ggg-ccc-atg-gaa-c | 5452-5467 |
| Nos-EcoRI-m | gtg-aat-tcg-atc-tag-taa-cat-aga-tga-cac-c | |
| Tad23-p | ggg-aaa-aat-agt-agt-aat-gat-cgg-tca-gtg-ccg-aac-aag-aac | 5499-5540 |
| Apa-m | tgg-gcc-cct-acc-ggg-ggt-aa | 6376-6395 |

Expression of DHFR-M2e Fusion Protein in *E. coli* and Production of Corresponding Antiserum.

Figure 2:
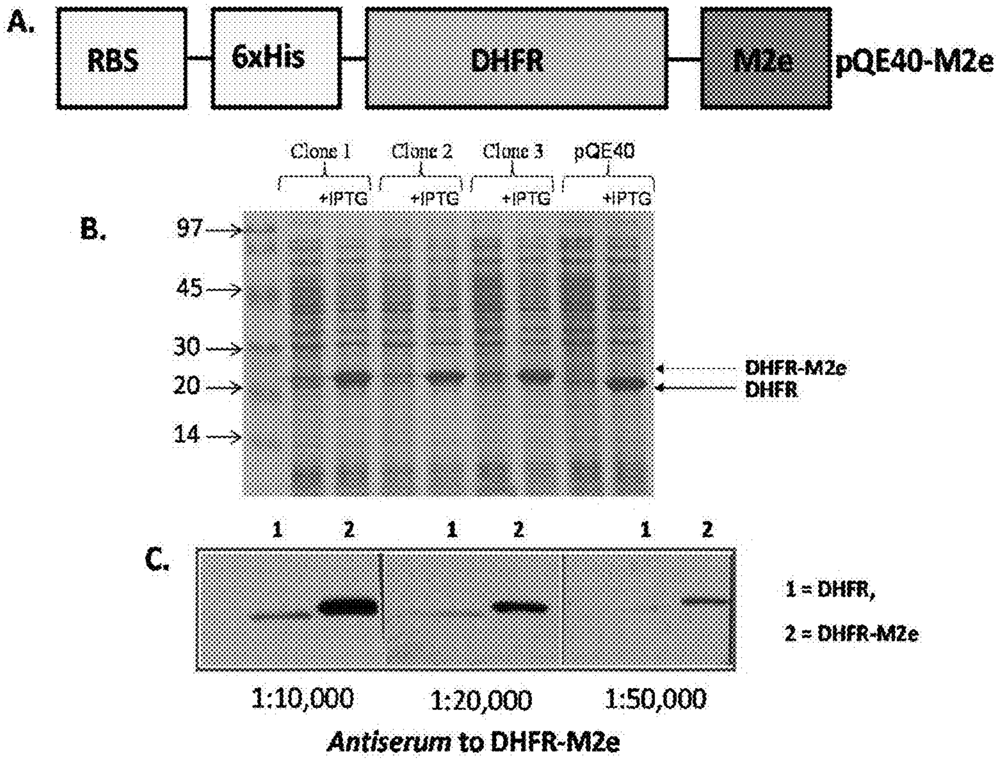
FIG. 2 shows the expression of the DHFR-M2e fusion protein in *E. coli* and testing of corresponding antiserum (AS). A. Layout of principal elements in plasmid construct used for expression in *E. coli*. RBS—ribosome-binding site, 6×His—affinity purification tag. B. Coomassie staining of total protein from *E. coli* with and without the addition of IPTG. Three independent pQE40-M2e clones (No. 1-3) were analyzed. The *E. coli* strain carrying expression vector pQE-40 and producing DHFR protein was used as a positive control. C. Western blotting analysis of the two expressed proteins using AS to DHFR-M2e. Each lane represents 100 ng of purified protein. Positions of molecular weight markers are indicated by arrows. AS was raised in mice after 3 consecutive injections with 100 μg of purified protein.

The M2e sequence was amplified with the use of the specific primers M2e-p, M2e-m, pQE-M2e-Bam-p and pQE-M2e-Hind-m. Subsequently, the PCR fragment was digested with BamHI and HindIII and then cloned into the pQE40 expression vector (QIAGEN, Germany) in frame with the mouse dihydrofolate reductase (DHFR) gene. The resulting fusion protein carried an antigen sequence at the C-terminus and 6×His tag at the N-terminus (FIG. 2A). DHFR-M2e (pQE40-M2e) and DHFR (pQE40) proteins were expressed in *E. coli* strain XL-1 Blue, induction was performed by adding IPTG to a 2 mM final concentration and total protein was analyzed in a 15% (w/v) reducing SDS-PAGE gel (FIG. 2B). DHFR-M2e and DHFR proteins were purified using Ni-NTA agarose column according to the manufacturer's protocol (QIAGEN, Germany). Dialysis of the recombinant protein against tri-distilled water was performed at room temperature and the protein was used for intraperitoneal immunization of mice (3 times, 100 μg per mouse at 2-week intervals). The resulting antiserum (AS) was used in subsequent experiments.

Cloning of Recombinant TMV-M2e Viral Vectors.

The pTMV-M2e-cys vector was generated through several PCR rounds. In round I, the subclone pA4083 was used as a template with primers Nco-mp-p and CP-154-m in order to synthesize the first PCR product. In round II, the second M2e-specific fragment was amplified from the vector pQE40-M2e with oligonucleotides CP-M2e-p and CP-M2e-m. In round III, the third PCR product was obtained with primers CP-155-p and Nos-EcoRI-m using plasmid pA4083 as a template again. In the final round, these PCR fragments were mixed to serve as a template for overlap PCR with primers Tad23-p and Apa-m. We performed all PCR reactions with Taq/Pfu enzyme mix (160:1) according to the "hot start" protocol.

The final PCR product, containing the TMV CP gene and M2e sequence, was digested with BsrGI/BstBI and inserted into the corresponding sites of pA4083 in order to replace the wild-type CP sequence. The intermediate construct pA4083-M2e was sequenced and two point mutations were found in the inserted DNA fragment that did not result in amino acid substitutions: A to G mutation in the CP gene (6032 nt in TMV-U1 genome) and C to T mutation in the 3'-NTR (6345 nt in TMV-U1 genome).

Vectors pTMV-M2e-ser and pTMV-M2e-ala were generated by two rounds of PCR. The first fragment was obtained with primers Tad23-p and CP-M2e-ser-m or CP-M2e-ala-m, respectively, the second fragment with primers CP-M2e-p and Apa-m; pA4083-M2e served as a template. Next, two PCR products for each set (Ser or Ala) were mixed and formed a template for overlap PCR with primers Tad23-p and Apa-m. These PCR products, which carried amino acid substitutions (Cys/Ser or Cys/Ala) within the consensus sequence of the human M2e epitope, were digested with BsrGI/BstBI and then cloned into the pA4083 vector. The modified region of the CP gene from each clone was verified by DNA sequencing. All three subclones were digested with BamHI/SalI and the smaller fragment was cloned into the binary vector pTMV-5' between the left and right borders of T-DNA such that it was under the control of Actin 2 promoter from *Arabidopsis thaliana* and the nos terminator. Thus, viral vectors pTMV-M2e-cys, pTMV-M2e-ser and pTMV-M2e-ala contained the sequences specifying three versions of the M2e immunogenic epitope (SLLTEVETPIRNEWGCRCNDSSD (SEQ ID NO:1), SLLTEVETPIRNEWGSRSNDSSD (SEQ ID NO:2), SLLTEVETPIRNEWGARANDSSD (SEQ ID NO:3), respectively) from human influenza A inserted between amino acids 155 and 156 of the TMV CP (FIG. 1). The binary vector pTMV-wt containing a full-length genome of wild-type TMV-U1 was used as a control (data not shown).

Virus Purification.

Agroinfiltration was performed as described previously using a modified (10 mM MES pH 5.6, 10 mM $MgSO_4$) resuspension buffer. Upper leaves of *Nicotiana benthamiana* systemically infected with each version of recombinant TMV-M2e were processed for virus purification. Leaf tissue (10-30 g) was homogenized in 2 volumes of 0.1 M sodium phosphate buffer (pH 7.0) and the extracts were clarified by centrifugation at 13,000 g for 10 mM. Supernatants were mixed with 0.25 volume of chloroform, shaken and centrifuged (13,000 g, 5 min). PEG/NaCl was added to the aqueous phase to a final concentration of 4%/1% (w/v), respectively, and the mixture was incubated overnight at 4° C. After centrifugation (13,000 g for 10 min), the pellet was resuspended in 0.01 M sodium phosphate buffer, pH 7.0. For further purification, the virus was collected by an additional cycle of ultracentrifugation (100,000 g, 2.5 hours (h), 4° C.) and resuspended in 0.01 M sodium phosphate buffer again.

For immunogold experiments, chimeric viruses TMV-M2e-ser and TMV-M2e-ala were purified as follows: systemically infected leaves were homogenized in 50 mM sodium phosphate buffer (pH 7.0) at the ratio of 1.5 ml/g of leaf material. The homogenate was centrifuged at 5,000 g for 20 mM, and the supernatant was mixed with 5% (w/v) diatomaceous earth and clarified at 12,000 g for 30 mM at 4° C. Chimeric viruses in the supernatant were pelleted by ultracentrifugation at 90,000 g for 90 mM Thereafter, the supernatant was removed and the pellet was resuspended in 1× phosphate-buffered saline (PBS).

The composition of proteins in the particle preparations was analyzed in 15% (w/v) reducing SDS-PAGE gels. The relative abundance of the proteins on Coomassie stained gels was calculated by Image J 1.44p software.

The absorbance of preparations of TMV-M2e samples in 10 mM sodium phosphate buffer (pH 7.0) were measured using a Hitachi U-2900 spectrophotometer (1 cm cuvettes). Absorbance due to light scattering was subtracted from the spectra. To calculate the concentrations of chimeric viral particles an absorption coefficient of 2.3 was used.

Once purified, TMV-M2e-ser and TMV-M2e-ala preparations were filtered through a 0.45 μM membrane (SARSTEDT, Germany); the samples can be stored (4° C.) for at least several months.

RNA Isolation and RT-PCR.

Preparations of samples of virus particles in 0.01 M Tris-HCl, 0.005 M EDTA pH 8.0 were mixed with 10% (w/v) SDS (1/20 volume to a final concentration of 0.5% (w/v)), 1 volume of buffer-saturated (0.01 M Tris-HCl, pH 8.0) phenol and 0.25 volumes of chloroform. After centrifugation (13,000 g, 20 min, 4° C.) RNA from the water phase was precipitated by the addition of three volumes of 96% ethanol and 0.1 volumes of 3 M sodium acetate (pH 5.0). The RNA pellet was resuspended in tri-distilled water.

Purified RNA was mixed with 15 pmol of specific primer (annealing at 75° C., 5 mM). Then 1× buffer (Fermentas) for reverse transcription (RT), dNTPs to a 0.5 mM final concentration, 2.5 mM $MgCl_2$, 20 units of RNase Inhibitor (Fermentas) and 200 units of Mu-MLV (Fermentas) were added and incubated for 5 minutes at 28° C. Reactions were performed at 37° C. for two hours. 1/10 of RT reaction volume was used as a template for following PCR analysis.

Immunogold Labeling and Electron Microscopy.

Purified virus particles at concentrations of 5-10 mg/ml were applied to carbon-coated copper EM grids (Ted Pella, USA) and left to settle for 1-2 mM. The grids were then blocked with 0.1% (w/v) bovine serum albumin (BSA) solution in 1×PBS containing 0.1% (v/v) Tween 20 for 15 minutes. Thereafter, mouse anti-DHFR-M2e serum (diluted 1:1000 in 1×PBS with 0.1% (v/v) Tween 20 containing 0.1% (w/v) BSA) was added and incubated for 1 hour followed by 3 washes for 15 mM with 50 μl of 1×PBS with 0.1% (v/v) Tween 20. The secondary goat anti-mouse antibodies conjugated with 6 nm gold particles (Jackson ImmunoResearch Laboratories, USA, 115-195-071) were diluted 1:50 in 1×PBS containing 0.1% (w/v) BSA and 0.1% (v/v) Tween 20. They were added to the grid at room temperature and incubated for 1 h. The grids were washed three times with 50 μl of 1×PBS plus 0.1% (v/v) Tween 20 for 15 min followed by 1 wash with water for 15 mM to remove excess antibodies. The grids were then negatively stained with the 1.5% (w/v) phosphotungstic acid solution (pH 6.0) for 2 minutes and examined using a JEOL JEM-1011 electron microscope with Gatan ES 500W Erlangshen digital camera and Digital Micrograph 1.85 software.

Western Blotting.

Proteins were separated by reducing SDS-PAGE on 15% (w/v) acrylamide gels and electro-transferred overnight at constant current (30 mA) to a PVDF membrane (Hybond P, Amersham). Subsequently, the membrane was blocked with Tris-buffered saline (TBS)-Tween 20 (T) (150 mM NaCl, 10 mM Tris-HCl, 0.1% (v/v) Tween 20, pH 8.0 containing 5% (w/v) nonfat dry milk ("Difco", USA) at room temperature for 1 h and then incubated with either rabbit anti-TMV CP (Department of Virology, Lomonosov Moscow State University, obtained after three intramuscular immunizations, 500 μg of protein per injection, two-week intervals; dilution 1:5000) or mouse anti-DHFR-M2e (dilution 1:15000) antibodies in 2.5% (w/v) milk/TBS-T for 1 h. After washing with TBS-T, the membrane was incubated for 1 h with anti-rabbit or anti-mouse horseradish peroxidase (HRP)-conjugated secondary antibodies (Sigma A6154 and A4416, respectively, dilution 1:15000). Signals were generated by chemiluminescence and documented on Hyperfilm (ECL detection system, Amersham). When needed, densitometric analysis of Western blots was performed with Image J 1.44p software.

Indirect ELISA.

Two hundred ng of antigen proteins (DHFR, DHFR-M2e) and viral particles (TMV-wt, TMV-M2e-ser and TMV-M2e-ala) diluted in 1×PBS (200 μl) were coated overnight at 4° C. on microtiter plates (Nunc MaxiSorp, Denmark). Following 5 washes with 1×PBS/0.1% (v/v) Tween 20, the plates were blocked with 2% (w/v) bovine serum albumin (BSA) in 1×PBS supplemented with 0.1% (v/v) Tween 20. The plates were incubated for 2 h at room temperature, then washed 5 times with 1×PBS/0.1% (v/v) Tween 20 and loaded with mouse antiserum raised against TMV-M2e-ala or TMV-M2e-ser (dilution 1:15000). Mouse antiserum against TMV-wt (Department of Virology, Lomonosov Moscow State University, obtained after three intraperitoneal immunizations, 100 μg of purified virus per injection, two-week intervals; dilution 1:15000) was used to control the immunogenicity of wild type TMV virus particles. All antibodies were diluted in 1×PBS buffer with 0.1% (v/v) Tween 20. The plates then were incubated for 2 h at room temperature, washed 5 times with 1×PBS/0.1% (v/v) Tween 20 and treated with 1:10000 dilution of secondary goat anti-mouse antibodies conjugated with HRP (Sigma A4416) for 1 h at 37° C. The plates were washed 5 times with 1×PBS/0.1% (v/v) Tween 20, and the 0.04% w/v ABTS (MP Biomedicals, France) substrate solution in 50 mM phosphate-citrate buffer with 0.009% (v/v) $H_2O_2$ was added to each well. The enzymatic reaction was measured after 40 min and optical densities were documented at 405 nm.

Immunization of Mice.

Female BALB/c mice (16-18 g) were obtained from the Institute of Animal Care (Pushchino, Russia). The mice were retained for 2 weeks in animal quarters and were immunized at the age of 8 weeks. Groups of 11 mice were immunized intraperitonial (i.p.) on the days 0 (primary), 14 (first boost), 28 (second boost) with 50 μg (total volume 100 μl) of TMV-M2e-ser, TMV-M2e-ala in the incomplete Freund's adjuvant. PBS buffer served as a negative control.

Blood samples (four pools composed of 5-6 mice from each group) were collected from ventral vein 2 weeks after the first and second boosts. Serum from the mice immunized with TMV-M2e-ala was also collected 7 months past the second boost.

Synthetic Peptides

The following synthetic peptides (G-18 and G-26) were tested as positive controls in the ELISA experiments:

```
G-18
                                   (SEQ ID NO: 1)
SLLTEVETPIRNEWGCRCNDSSD (M2e, human consensus)

A/PR/8/34
                                   (SEQ ID NO: 19)
SLLTEVETPIRNEWGCRCNGSSD (M2e, A/PR/8/34, H1N1)

G-26
                                   (SEQ ID NO: 20)
SLLTEVETPTRSEWECRCSDSSD (M2e, A/California/04/
2009, H1N1)
```

Residues that differ between the sequences are displayed in bold font and underlined. M2e sequence of influenza virus A/PR/8/34 is presented for comparison.

Antibodies Detection in the Sera.

M2e-specific IgG levels were determined by ELISA in 96-well microtiter plates ("Greiner", Germany) coated overnight at 4° C. with the M2e peptide (G-18, G-26) in PBS (5 μg/ml) 100 μl/well. The plates were blocked with PBS containing 5% (v/v) fetal calf serum (FCS) 300 μl/well for 1 h at room temperature. Then the plates were washed 3 times in PBS-T (0.1% (v/v) Tween-20. Sera were serially diluted by PBS with 5% (v/v) FCS. The diluted samples (100 μl/well) were added and the plates were incubated 1 h at room temperature. The plates were washed 3 times in PBS-T. For detection of IgG subclasses, HRP-labeled rabbit anti-mouse IgG antibodies (Abcam, UK, ab6728), biotinylated rat anti-mouse IgG1 and IgG2 antibodies (BD Pharmingen, 553441 and 553388) and streptavidin conjugated with HRP (BD Pharmingen, 554066) were diluted in PBS with 5% (v/v) FCS and added (100 μl/well) into the plates. Incubation was performed at room temperature for 1 h. Final washing was carried out 4 times in PBS-T. The plates were developed with the TMB substrate reagent set (BD Pharmingen, 555214) according to manufacturer's recommendations. Reaction was stopped by 50 μl 2M $H_2SO_4$ and $OD_{450}$ was measured on a Bio-Rad xMark microplate spectrophotometer. ELISA endpoint titers were defined as a reciprocal of the highest dilution yielding an $OD_{450}$ value 2 times above the mean value of the negative control wells.

MDCK Whole Cell ELISA.

Sera to TMV-M2e-ser and TMV-M2e-ala were tested for reactivity with MDCK (Madin-Darby Canine Kidney) epithelial cells (received from the Russian Collection of Vertebrate Cell Cultures, Institute of Cytology RAS, Saint-Petersburg, Russia) infected by influenza A as reported previously [14]. The MDCK cells were cultured with DMEM medium (Paneco, Russia) containing 5% (v/v) FCS until they became confluent. The cells were then incubated overnight at 37° C. with $10^6$ egg infective dose (EID) of influenza virus A/PR/8/34 or with medium alone (uninfected control). Subsequently, the plates were washed with PBS and fixed for 10 min at room temperature by 10% (v/v) formaldehyde. After that, the plates were washed 3 times with PBS and blocked with PBS+5% FCS for 1 h at room temperature. Serial dilutions of the sera to either TMV-M2e-ser or TMV-M2e-ala were added to the cells and incubated for 1 h. Wells were washed and incubated with HRP-labeled rabbit anti-mouse IgG antibodies (Abcam, UK, ab6728) for 1 h at room temperature, followed by the TMB substrate Reagent Set (BD Bioscience, 555214) for 15 min—at room temperature as well. The reaction was stopped by the addition of 50 μl 2M $H_2SO_4$ and $OD_{450}$ was measured on a Bio-Rad xMark microplate spectrophotometer. The data reflected the mean ΔOD (infected-uninfected cells) of triplicate wells per sample.

Virus Challenge.

The mice (n=11/group) were challenged intranasally 2 weeks after the final immunization with sublethal ($1LD_{50}$) and lethal ($5LD_{50}$) doses of homologous (A/PR/8/34) and heterologous (A/California/04/2009) influenza viruses. Influenza virus A/PR/8/34 (H1N1) was taken from the Collection of Acute Respiratory Infection Viruses (Research Institute of Influenza, Ministry of Health of the Russian Federation, St. Petersburg, Russia). Influenza virus A/California/04/2009 (H1N1) was received from the Center for Disease Control and Prevention (Atlanta, USA). Mice were anesthetized by intraperitoneal injection of 0.1 ml/20 g xylazine/zoletil 100 (1 ml 2% xylazine, 2 ml 10% zoletil, 7 ml PBS). Mice immunized with PBS were challenged as a negative control. The animals were monitored daily for 2 weeks for survival, weight loss and clinical presentation. Clinical scores were assigned as follows: 4 pts—healthy, 3 pts—reduced grooming, 2 pts—reduced physical activity and 1 pts—moribund.

Statistical Analysis.

The difference between antibody levels was evaluated by the Mann-Whitney U-test. The life length evaluation was assessed by instantaneous sampling (Kaplan-Meyer). Significant differences in survival among mouse groups were analyzed by the Mantel-Cox (log-rank) and Gehan-Breslow-Wilcoxon tests. The difference in weight loss and clinical scores was evaluated by GraphPad Prismv.

Results

Example 1

Viral Vectors TMV-M2e Cause Systemic Infections of *Nicotiana benthamiana*

Following agroinfiltration, TMV-M2e-cys, TMV-M2e-ser and TMV-M2e-ala (FIG. 1), containing the full-length TMV-U1 genome with different versions of M2e coding sequence, were all able to spread via the vascular system of infected *Nicotiana benthamiana* plants. Reverse transcription and subsequent PCR analysis of RNA extracted from purified virions proved that all the recombinant genomes were genetically stable. Analyses of the progeny of the secondary infection did not reveal any reversion to the wild-type TMV (data not shown). Non-inoculated systemic leaves were taken for purification of TMV-M2e chimeric viral particles.

Example 2

Antiserum to DHFR-M2e Contains High-Titer Antibodies Against Influenza Epitope Analysis of mouse polyclonal antiserum (AS) produced against the purified DHFR-M2e fusion protein by Western blotting revealed a high titer of M2e-specific antibodies as compared to antibodies against the carrier (DHFR); cross-reaction of the antiserum with DHFR protein (100 μg) was significantly less than with DHFR-M2e (FIG. 2C). A working dilution of 1:50000 virtually abolished the DHFR-specific signal, while the signal against the epitope was still readily detectable. Therefore, AS to DHFR-M2e taken at 1:50000 could be regarded as AS specific for the M2e epitope. It has been found that the C-terminal location of M2e epitope within the DHFR-M2e fusion protein was quite efficient for inducing specific antibodies. This antiserum was used for the detection of the M2e epitope by Western blots and immunogold labeling of chimeric viral particles.

Example 3

Characterization of Recombinant Virions

TMV-M2e particles were purified from plant extracts by PEG precipitation followed by low-speed centrifugation (10,000 g) and ultracentrifugation (100,000 g). Proteins from the purified chimeric viral particles were separated on 15% (w/v) reducing acrylamide gels and stained with Coomassie brilliant blue. This analysis showed that the method used to isolate particles from the TMV-M2e-cys extract resulted in the isolation of virions lacking M2e epitope (FIG. 3A, lane 1).

Figure 3:
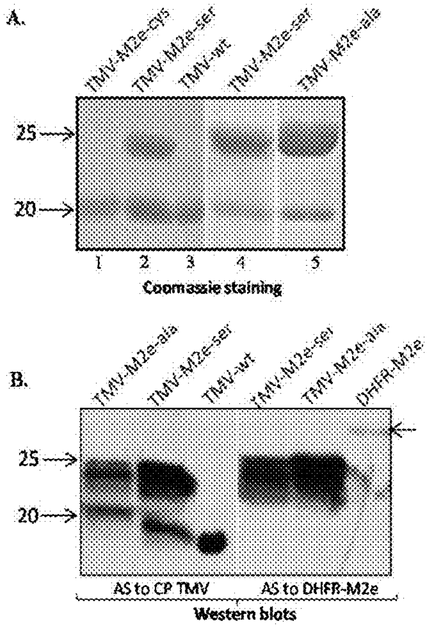
FIG. 3 shows gels of CP from purified chimeric virions isolated from systemically infected leaves of *Nicotiana benthamiana*. A. SDS-PAGE with Coomassie staining of the CP from isolated chimeric viruses. B. Western blotting of viral preparations with antiserum (AS) to CP TMV and DHFR-M2e. Positive controls: TMV-wt and DHFR-M2e. Positions of molecular weight markers are indicated by arrows.

Two main proteins with electrophoretic mobilities of about 20 and 24 kDa, were identified in the TMV-M2e-ser and TMV-M2e-ala preparations; these sizes correlate with the predicted molecular weight of the wt CP and CP-M2e fusion protein, respectively (FIG. 3A, lanes 1-3). Western blotting of proteins from purified chimeric particles demonstrated that the 24 kDa protein was the only one which reacts with antiserum to the M2e epitope. Antiserum to TMV coat protein (CP) reacted with both CP and chimeric proteins (FIG. 3B). Therefore, the preparations of TMV-M2e-ser and TMV-M2e-ala particles isolated from systemically infected leaves contained both variants of CP: with and without M2e. The ratio between the quantities of two proteins differed depending on the age of plants, duration of infections, and the presence or absence of symptoms on the systemically infected leaves. The lowest registrated amount of chimeric target 24 kDa protein was about 50% (FIG. 3A, lane 2), while the standard CP-M2e protein accumulation reached 80-90% of the total protein preparation (FIG. 3A, lanes 4, 5). We did not observe a significant difference between TMV-M2e-ser and TMV-M2e-ala in respect to the 24:20 kDa protein ratio. Neither of the mutants gave preparations that contained only the 24 kDa protein without its 20 kDa counterpart. A certain proportion of the 20 kDa protein may be important for efficient assembly of chimeric particles. On the other hand, the immunoelectron microscopy showed the presence of some distinct particles that did not react with M2e-specific primary antibodies (FIG. 4C), indicating that they did not contain any CP-M2e fusion protein. Periodically, additional minor bands located between the 20 and 24 kDa proteins were detected in the preparations (FIG. 3A, lanes 4, 5). Most probably, the production of these bands was due to a partial proteolytic trimming of M2e peptide and/or C-terminal amino acids of TMV CP (aa 156-159 in our TMV-U1 isolate). Taking into consideration the genetic stability of all TMV-M2e vectors, we conclude that the shortened 20 kDa protein emerges after the cleavage of C-terminal M2e antigen; this might happen either before the assembly of chimeric virions or upon completion of this process.

Example 4

Immunogold Labeling and Electron Microscopy of Chimeric Viral Particles

The location of the M2e epitopes on the surface of the purified TMV-M2e-ser and TMV-M2e-ala virions was examined more closely using immunoelectron microscopy with gold-labeled secondary antibodies. This demonstrated that numerous M2e epitopes were exposed on the surface of the recombinant virus particles (FIG. 4A, B, C). Wild-type TMV served as a negative control which reacted with neither the primary nor secondary antibodies (FIG. 4D). Electron microscopy also showed that the foreign M2e epitopes were tightly packed and uniformly distributed on the surface of the chimeric virions. It was possible to distinguish the shape of TMV-M2e-ser and TMV-M2e-ala virions from each other after immunogold labeling. TMV-M2e-ser looked somewhat sloppy and bound more phosphotungstic acid on the sides of the particles, thus resulting in higher electron density. This might be due to different charges on the surface of TMV-M2e-ser and TMV-M2e-ala particles which were caused by a putative phosphorylation of serine residues in the M2e-ser peptide.

Example 5

The Antisera to Chimeric Particles React Much More Efficiently with M2e Epitopes than with the TMV CP Carrier Western Blotting.

Figure 5:
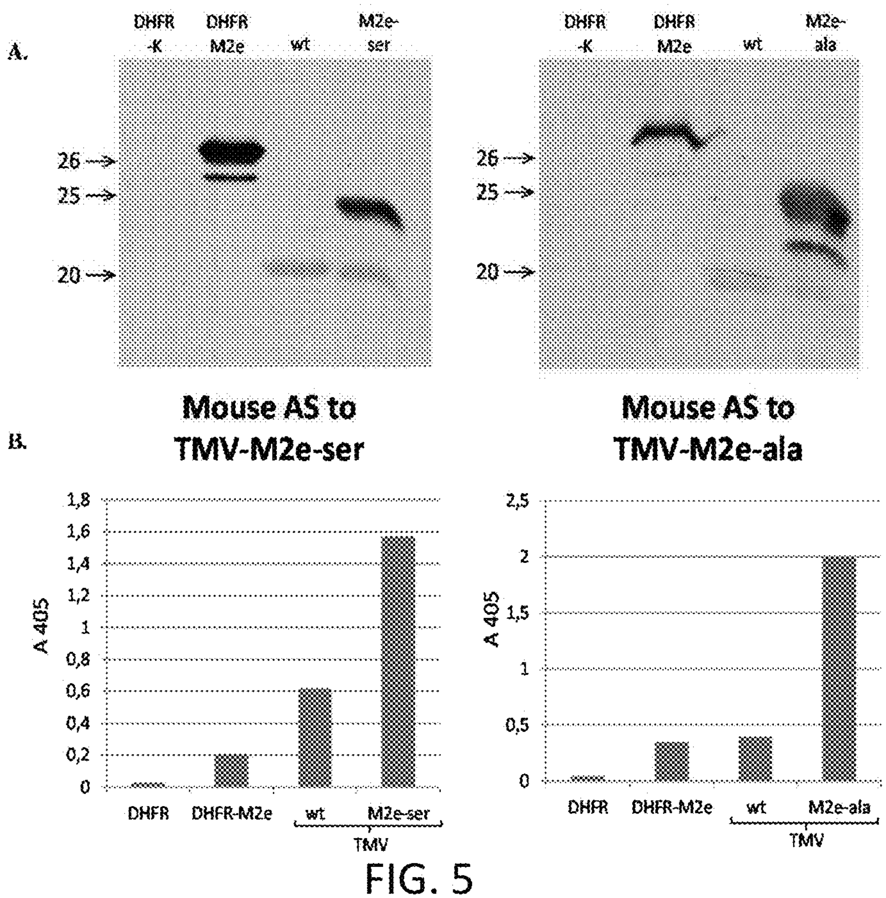
FIG. 5 shows the ratios of antibody titers to M2e epitope and to its carrier (TMV). At the top (A): testing of antibodies by Western blottings of purified chimeric viruses and control proteins. Positions of molecular weight markers are indicated by arrows. At the bottom (B): characterization of antibodies specific to M2e epitopes and to TMV carrier by indirect ELISA. Both antisera were diluted 1:15000. Result of a typical experiment is shown. Ordinate axes show absorbance measured at 405 nm.

The antisera to chimeric particles were used in Western blotting experiments with chimeric virions and wild-type (wt) TMV. DHFR and DHFR-M2e proteins served as controls. Three pools of each serum, specific either to TMV-M2e-ser or to TMV-M2e-ala obtained after the 3rd immunization, were mixed at a working dilution for both sera of 1:15000 and 200 ng of the proteins and viral preparations were examined (FIG. 5). DHFR-M2e protein gave a strong signal comparable with the one seen with either version of TMV-M2e. Both chimeric CP-M2e proteins reacted intensely whereas TMV-wt CP displayed a weak signal, providing evidence in support of the assumption that the majority of TMV CP epitopes in chimeric TMV-M2e particles are hidden from the immune system by the M2e epitopes exposed on their surface. We can also assume that TMV-M2e-ser and TMV-M2e-ala recombinant particles remain stable in the blood and lymphatic flow during the immunization. It should be noted that the additional minor band appearing between the 20 and 25 kDa protein markers on the Western blot of TMV-M2e-ala preparation (FIG. 5) most probably corresponds to the band visible on Coomassie stained gel displaying proteins from the purified TMV-M2e-ala particles (FIG. 3A, lane 5). According to the densitometry of Western blots, the ratio between antibodies against the epitope and carrier is approximately 7:1 (data not shown).

ELISA Experiments.

Figure 4:
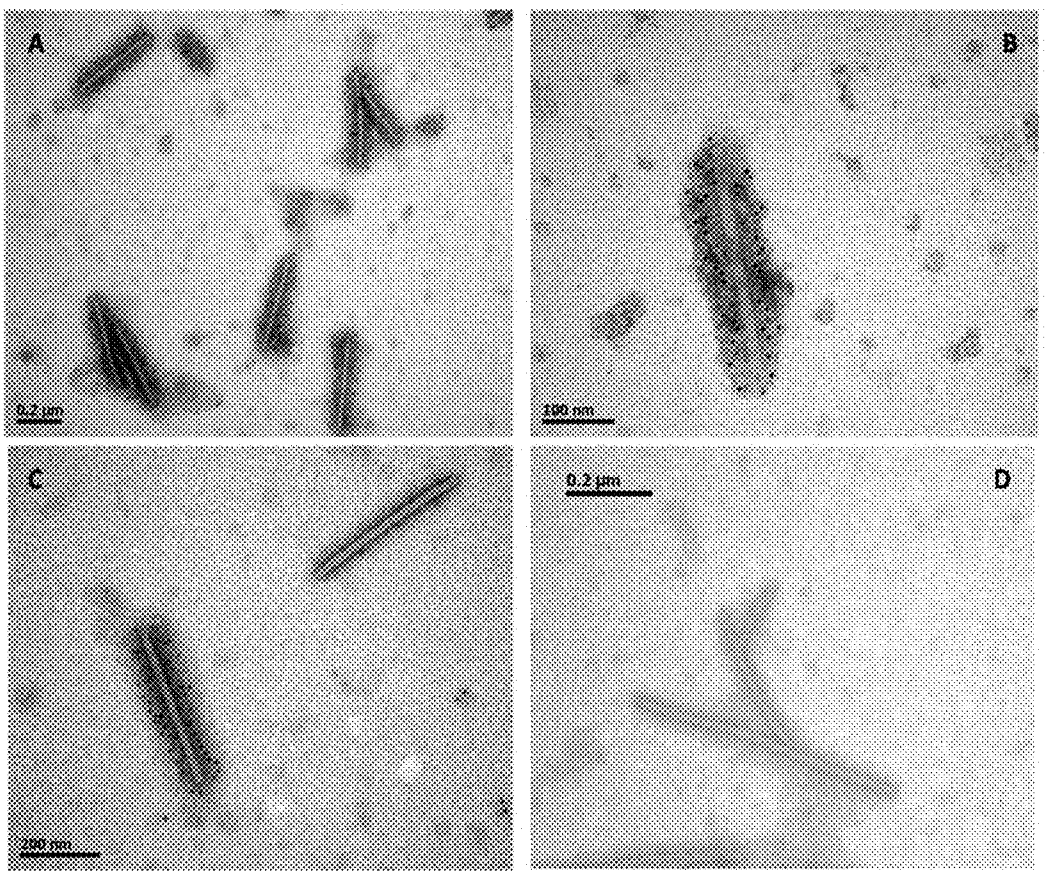
FIG. 4 shows immunogold labeling of purified chimeric viruses. A,C—TMV-M2e-ala; B—TMV-M2e-ser; D—TMV-wt. Primary antibodies—against DHFR-M2e, secondary (anti-mouse) antibodies—conjugated with gold particles (6 nm). Magnifications: A—80,000; B—200,000; C—150,000; D—100,000. Scale bars are indicated.

Antisera to TMV-M2e-ser and TMV-M2e-ala particles were tested by indirect ELISA in order to compare the immunological properties of chimeric CP-M2e fusion proteins in native (ELISA) and denatured (Western blotting) states. DHFR, DHFR-M2e proteins, chimeric TMV virions and TMV-wt (200 ng each) were loaded into the wells of a microtiter plate and incubated with mouse antisera against TMV-M2e-ser and TMV-M2e-ala (FIG. 5), as well as TMV-wt and DHFR-M2e (data not shown). All AS were diluted as 1:15000. Incubation with HRP-labeled secondary antibodies was performed for 60 minutes. Background levels (antigen without primary antibodies) were subtracted throughout. FIG. 5 shows that the chimeric particles reacted strongly with antisera specific to TMV-M2e-ser or TMV-M2e-ala. The wild-type particles displayed a moderate reaction with the sera specific to TMV-M2e-ser or TMV-M2e-ala, the ratio of TMV-M2e-ser/TMV-wt and TMV-M2e-ala/TMV-wt measurements varied from 2.7:1 (TMV-M2e-ser) to 5:1 (TMV-M2e-ala) indicating that antibodies recognize the M2e epitopes on the surface of recombinant particles far more efficiently than the epitopes of the carrier itself. These observations were in line with the data obtained by Western blotting (FIG. 5). Therefore, comparative analyses of antisera suggested that TMV CP was somewhat less accessible to anti-CP antibodies in TMV-M2e-ala than in TMV-M2e-ser chimeric particles, which correlates with different structures seen in the electron microscope (FIG. 4). The Ala substitutions located on the surface of recombinant TMV-M2e particles may produce a more efficient immune response.

Example 6

Immunogenicity of TMV-M2e-Ser and TMV-M2e-Ala in Mice

Figure 6:
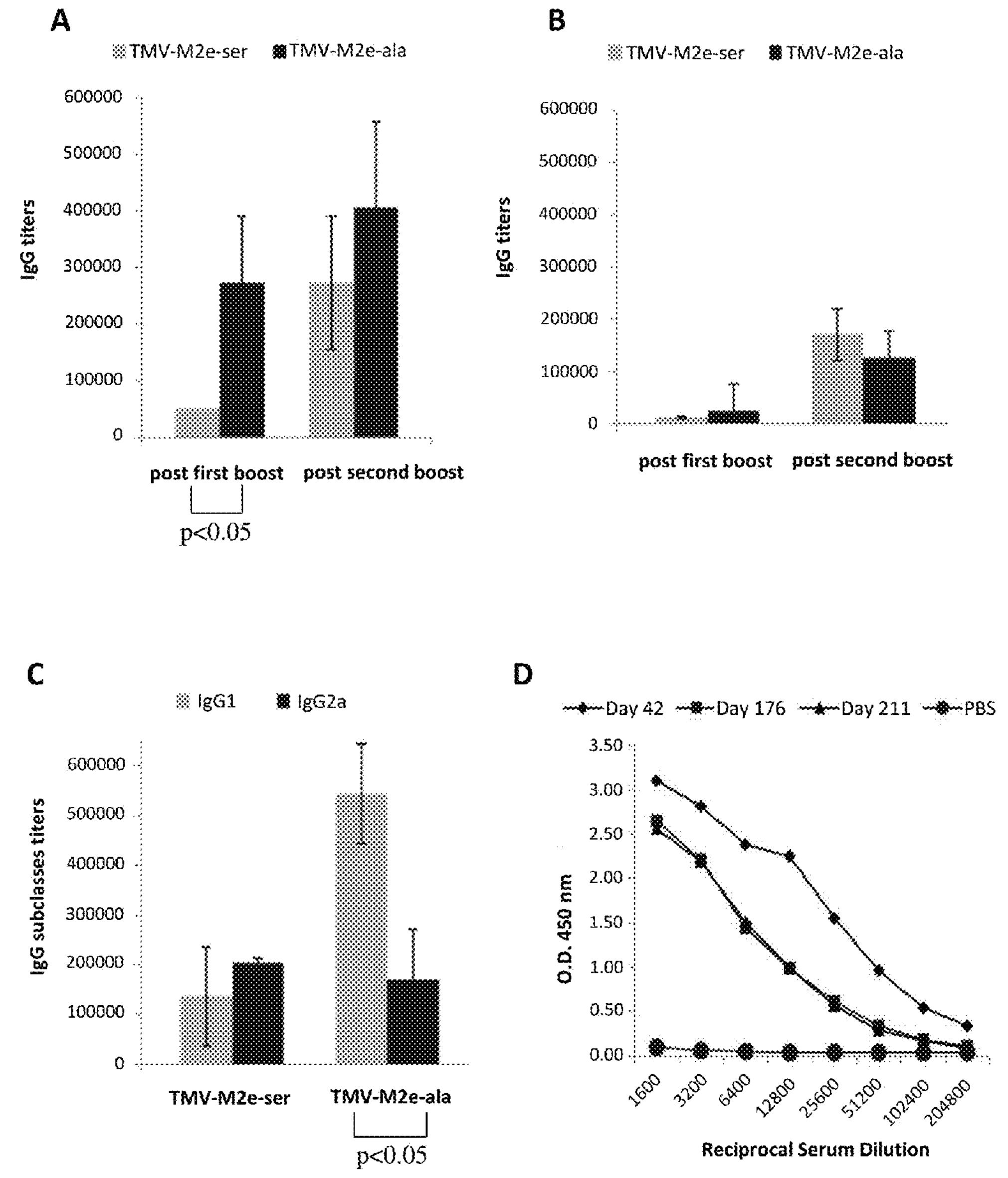
FIG. 6 shows the immunogenicity of TMV-M2e-ser and TMV-M2e-ala. BALB/c mice (n=11/group) were immunized intraperitoneally on days 0, 14, 28 with 50 μg of TMV-M2e-ser or TMV-M2e-ala. PBS was used as the negative control. Two weeks post first and second boost M2e-specific IgG responses were evaluated by ELISA to G-18 (A) and G-26 (B) synthetic peptides. Anti-M2e IgG titers in mice control group (PBS) were 1:200. Average values from four pools in each group are shown. (C) Anti-M2e IgG subclasses tested against G-18 in serum from TMV-M2e-ser and TMV-M2e-ala immunization groups 2 weeks post second boost were determined by ELISA. Average values from four pools in each group are shown. (D) Longevity of antibody response. M2e-specific serum IgG responses in TMV-M2e-ala immunization group to peptide G-18 were examined at 42, 176 and 211 days post second boost. It shall be noted that the curves for days 176 and 211 overlap along the dilution series.

The immunogenicity of chimeric virions in the presence of incomplete Freund's adjuvant was examined in BALB/c mice (n=11/group) immunized intraperitoneally on the days 0, 14, 28 with TMV-M2e-ser or TMV-M2e-ala particles. PBS served as a negative control. On days 28 and 42 the mice were bled and four pools of serum (5-6 mice sample) were subsequently tested for anti-M2e IgG, IgG1 and IgG2a by ELISA. On the day 28, the mice immunized with TMV-M2e-ala showed an interaction intensity of anti-M2e IgG with the homologous M2e synthetic peptide (G-18) significantly higher ($p<0.05$) than that from the mice immunized with TMV-M2e-ser (FIG. 6A). The interaction of anti-M2e IgG with the heterologous M2e synthetic peptide (G-26) was 4 and 1.5 times weaker in the mice immunized with TMV-M2e-ser and 10 and 3 times weaker in the mice immunized with TMV-M2e-ala on the days 28 and 42, respectively (FIG. 6B).

Also examined was the profiles of M2e-specific IgG subclasses in the mice immunized with TMV-M2e-ser and TMV-M2e-ala after the second boost (FIG. 6C). Almost equal levels of IgG1 and IgG2a were detected ($p<0.05$) in the mice immunized with TMV-M2e-ser (IgG1/IgG2a ratio of 0.7). The level of the IgG1 subclass in serum was somewhat higher than IgG2a ($p<0.05$) in the mice immunized with TMV-M2e-ala (IgG1/IgG2a ratio of 3.2). The titers of IgG1 in the mice immunized with TMV-M2e-ala were almost 4 times higher than in the mice immunized with TMV-M2e-ser; however, the titers of IgG2a were practically equal.

The longevity of M2e-specific IgG response was evaluated in BALB/c mice immunized with 50 μg TMV-M2e-ala on the days 0, 14, 28, and bled on the days 42, 176, 211 after the second boost. The results demonstrate that the anti-M2e IgG response declined insignificantly during the 7 month period (FIG. 6D).

Example 7

Figure 7:
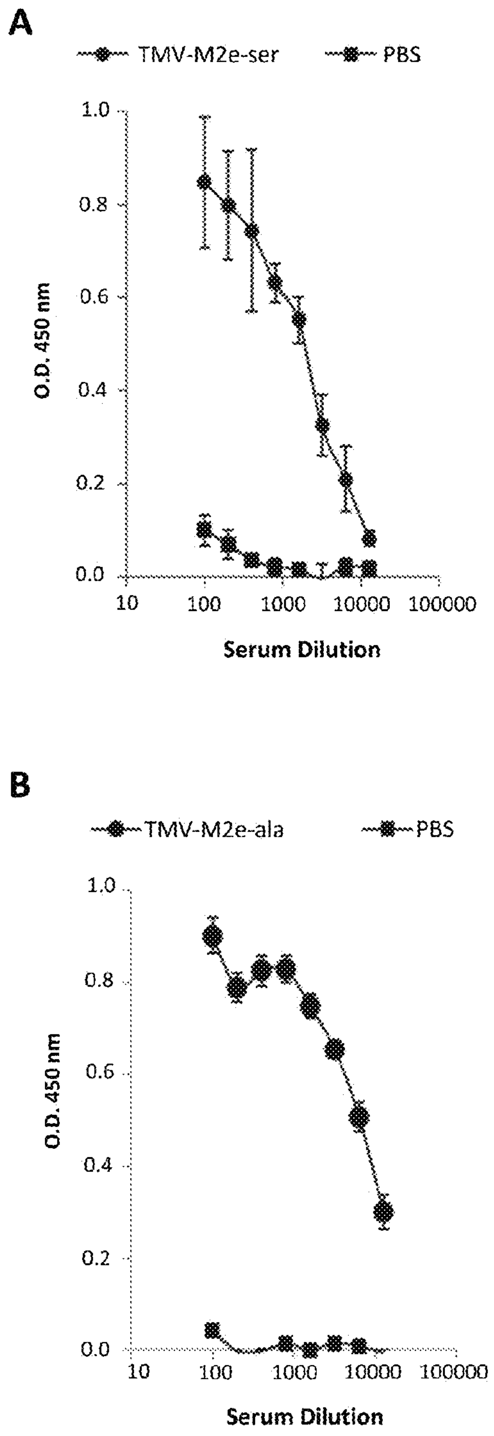
FIG. 7 shows the recognition of influenza-infected MDCK cells by antisera from TMV-M2e-ser (A) and TMV-M2e-ala (B) immunized mice. The PBS line refers to a control mice group, immunized intraperitoneally with PBS. Two weeks post second boost sera were tested for reactivity with control (inoculated with PBS) and A/PR/8/34 infected MDCK cells in vitro. Data represent the $\Delta OD_{450}$ (infected-uninfected cells).

The Antisera to TMV-M2e Recognize M2 Protein on the Surface of Epithelial Cells Infected with Influenza Virus The results presented above show that antibodies induced by TMV-M2e-ser and TMV-M2e-ala bind efficiently to a synthetic peptide corresponding to the consensus M2e sequence (G-18). In order to determine whether the anti-M2e antibodies recognize M2e epitope during natural infection, we used a MDCK whole cell ELISA assay. MDCK cells were grown in tissue culture plates, infected with A/PR/8/34 influenza virus, fixed and incubated with serial dilutions of immune and non-immune sera. The sera taken from the mice immunized with TMV-M2e-ser (FIG. 7A) and TMV-M2e-ala (FIG. 7B) bound specifically to the MDCK cells infected with the influenza A/PR/8/34 virus but not with cells inoculated with PBS. We, therefore, conclude that the TMV-M2e-ala and TMV-M2e-ser anti-M2e antibodies from the mice are capable of recognizing either the synthetic M2e peptide or native M2e epitope exposed on the surface of influenza virus-infected cells.

Example 8

TMV-M2e-Ser and TMV-M2e-Ala Confer Protection Against Homologous and Heterologous Virus Challenge The groups of 11 mice immunized with 50 μg (i.p. on the days 0, 14 and 28) of TMV-M2e-ser and TMV-M2e-ala in the incomplete Freund's adjuvant were challenged intranasally 2 weeks after the second boost with sublethal ($1LD/_{50}$) and lethal ($5LD/_{50}$) doses of homologous influenza virus A/PR/8/34 (H1N1) and lethal dose ($5LD/_{50}$) of heterologous influenza virus A/California/04/2009 (H1N1). Mice immunized with PBS were challenged as a negative control. After challenge the animals were monitored daily for survival, weight loss and clinical presentation over a period of 2 weeks.

Figure 8:
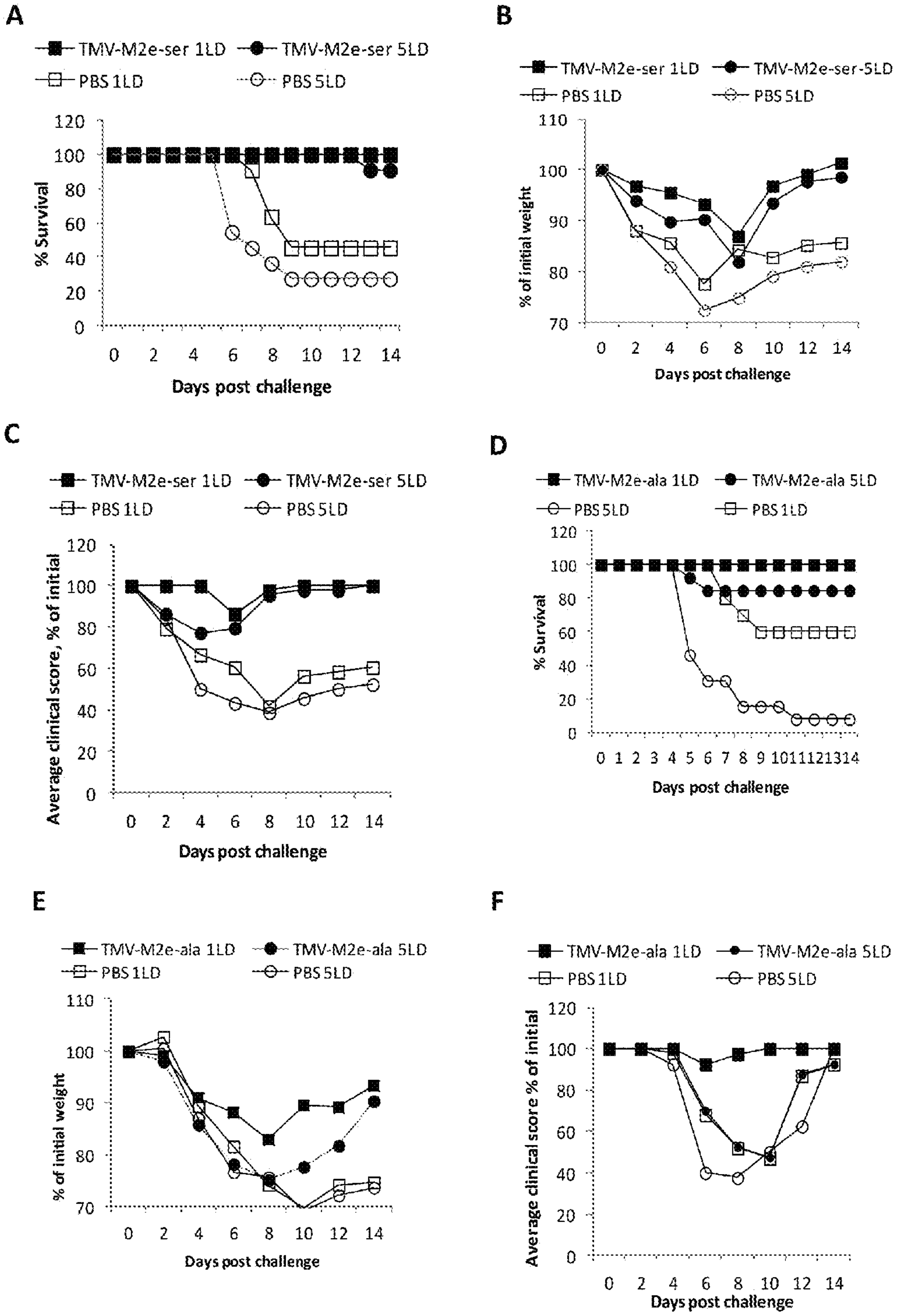
FIG. 8 shows the efficacy of TMV-M2e-ser (A,B,C) and TMV-M2e-ala (D,E,F) immunization in homologous challenge. BALB/c mice (n=11/group) were immunized with 50 μg of TMV-M2e-ser and TMV-M2e-ala on days 0, 14 and 28. On day 42 mice were challenged intranasally with $1LD_{50}$ and $5LD_{50}$ of influenza A/PR/8/34 (H1N1). (A,D) Survival rates (significant difference from control mice, $p<0.05$). (B,E) Loss of body weight after challenge (significant difference from control mice, $p<0.05$). (C,F) Clinical scores (significant difference from control mice, $p<0.05$).

As shown in FIG. 8A, all the mice (100%) treated with TMV-M2e-ser survived the sublethal homologous challenge and 90% of the animals survived the lethal homologous challenge (significant difference from control mice, $p<0.05$). The test mice were under observation for body weight loss and clinical score for 14 days after the challenge. The results demonstrated (FIG. 8 B,C) that the immunized mice experienced significantly lighter disease symptoms and weight loss than the naïve mice ($p<0.05$). The homologous challenge in the mice treated with TMV-M2e-ala showed similar results (FIG. 8D). The rate of survival among the mice after the sublethal homologous challenge was 100%, while the rate of survival among the mice after the lethal virus challenge was 84%. This demonstrated an enhanced survival of the immunized mice compared to the control animals ($p<0.05$). The mice immunized with TMV-M2e-ala showed significantly lighter clinical symptoms and weight loss after $1LD_{50}$ challenge compared to the control mice ($p<0.05$), but the differences in weight loss and clinical symptoms after $5LD_{50}$ challenge were statistically non-significant (FIG. 8E, F). It may be connected with the prevalence of IgG1 response, which is less effective than IgG2a in antibody-dependent cell-mediated cytotoxicity (ADCC).

Figure 9:
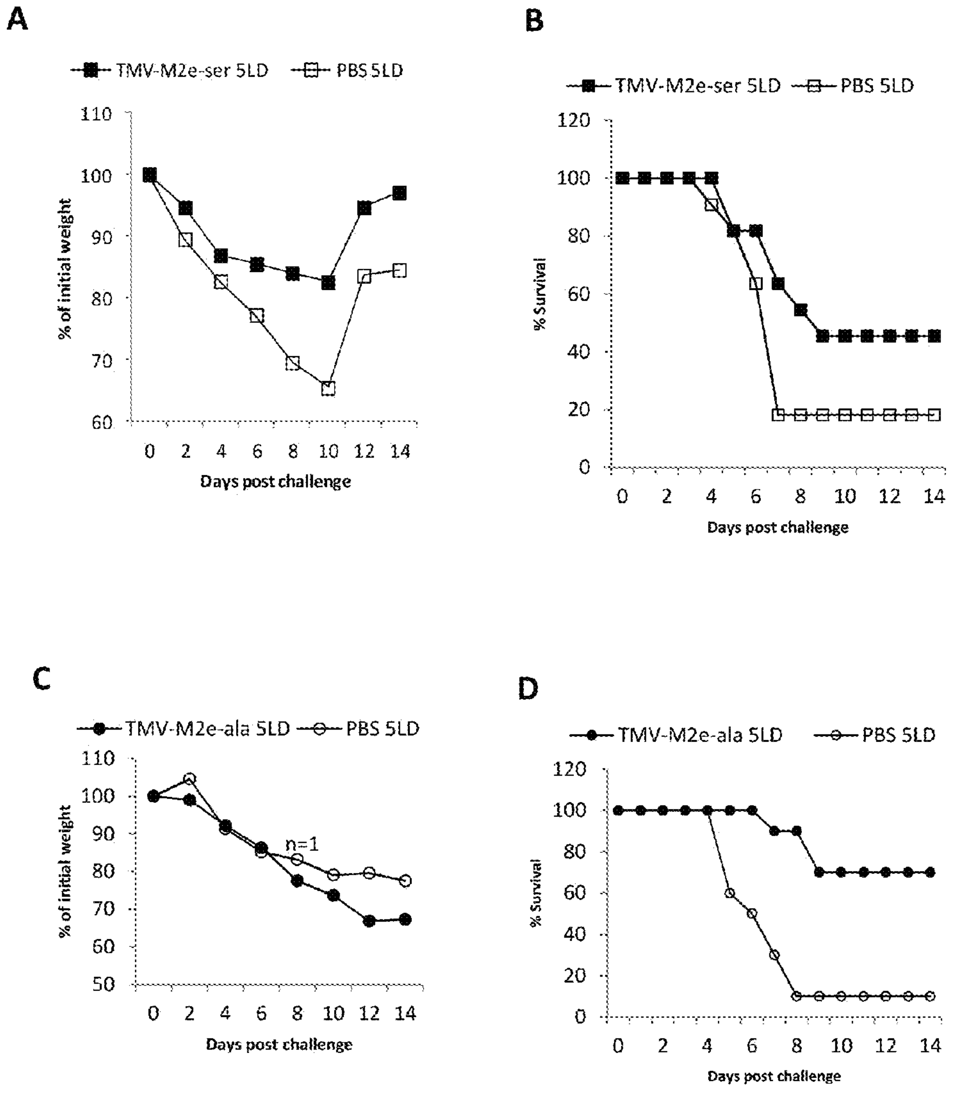
FIG. 9 shows the efficacy of TMV-M2e-ser and TMV-M2e-ala immunization in heterologous challenge. BALB/c mice were immunized with 50 μg of TMV-M2e-ser or TMV-M2e-ala on days 0, 14 and 28. On day 42 mice were challenged intranasally with $5LD_{50}$ of influenza A/California/04/2009 (H1N1). (A,C) Loss of body weight after challenge. (B,D) Survival rate (significant difference from control mice, $p<0.05$).

Despite the differences between the human consensus M2e and the M2e of A/California/04/2009 (H1N1) (4 amino acid residues), heterologous challenge with a lethal dose ($5LD_{50}$) of the influenza virus A/California/04/2009 (H1N1) showed that partial protection of the mice could be obtained by immunization with TMV-M2e-ser (46% of survival) and TMV-M2e-ala (70% of survival) (FIG. 9). The difference in survival rates of the immunized groups and control animals was statistically significant ($p<0.05$), unlike the differences in weight loss.

The invention claimed is:

1. A recombinant rigid, rod-shaped chimeric viral particle capable of replication in a plant cell comprising:

a fusion protein comprising:

a coat protein that is at least 80% identical to the amino acid sequence of a wild type Tobacco Mosaic Virus (TMV) coat protein, and the influenza A virus M2e epitope of SEQ ID NO: 1, except that the positions corresponding to cys17 and cys19 of SEQ ID NO:1 in the epitope are each independently substituted by a serine or alanine; and wherein said epitope is inserted into said coat protein between Ser155 and Gly156 of the TMV coat protein.

2. The viral particle of claim 1, wherein said particle has been produced by a plant cell.

3. The viral particle of claim 2, wherein said particle has been produced by a *Nicotiana benthamiana* plant.

4. A method of producing an immune response, comprising:

administering a recombinant rigid, rod-shaped viral particle of claim 1 to an animal, thereby causing the animal to produce antibodies that recognize said epitope.

5. The method of claim 4, wherein said administering protects against future infection by said human and/or animal pathogen.

6. The method of claim 4 wherein said viral particle is administered to said animal in conjunction with an adjuvant.

7. The method of claim 4, wherein the administering is parenterally, enterally or orally.

8. The viral particle of claim 1, wherein the amino acid sequence of said coat protein is identical to the TMV-U1 coat protein.

9. The viral particle of claim 1, wherein the positions corresponding to cys17 and cys19 of SEQ ID NO:1 in the epitope are each substituted by a serine.

10. The viral particle of claim 1, wherein the positions corresponding to cys17 and cys19 of SEQ ID NO:1 in the epitope are each substituted by an alanine.

* * * * *